US007790872B2

United States Patent
Higo et al.

(10) Patent No.: US 7,790,872 B2
(45) Date of Patent: Sep. 7, 2010

(54) RICE CATALASE B PROMOTER

(75) Inventors: Kenichi Higo, Tsukuba (JP); Masao Iwamoto, Tsukuba (JP); Hiromi Higo, Tsukuba (JP)

(73) Assignee: National Institute of Agrobiological Sciences (JP)

( * ) Notice: Subject to any disclaimer, the term of this patent is extended or adjusted under 35 U.S.C. 154(b) by 988 days.

(21) Appl. No.: 10/344,982

(22) PCT Filed: Jan. 25, 2002

(86) PCT No.: PCT/JP02/00573

§ 371 (c)(1),
(2), (4) Date: Feb. 18, 2003

(87) PCT Pub. No.: WO03/064649

PCT Pub. Date: Aug. 7, 2003

(65) Prior Publication Data

US 2006/0230470 A1    Oct. 12, 2006

(51) Int. Cl.
  *C07H 21/04*    (2006.01)
  *C12N 15/82*    (2006.01)
  *A01H 5/00*    (2006.01)
(52) U.S. Cl. ............... 536/24.1; 800/287; 800/278; 800/279; 800/288; 800/298
(58) Field of Classification Search ............... None
See application file for complete search history.

(56) References Cited

U.S. PATENT DOCUMENTS 6,774,282 B1 *    8/2004    Ritchie ............... 800/287

FOREIGN PATENT DOCUMENTS

| JP | 09-084587 | 3/1997 |
| WO | WO 01/81606 | 11/2001 |

OTHER PUBLICATIONS

Hemmings-Mieszczak et al. Alternative structures of the Cauliflower Mosaic Virus 35 S RNA leader: implications for viral expression and replication. (1997) J. Mol. Biol., vol. 267, pp. 1075-1088.*
Kenichi, H. Promotor of oryza sativa catB gene. (1997) JP 09-084587, pp. 1-13.*
Doelling et al. The minimal ribosomal RNA gene promoter of *Arabidopsis thaliana* includes a critical element at the transcription initiation site. (1995) The Plant Journal; vol. 8, pp. 683-692.*
Maiti et al. Promoter/leader deletion analysis and plant expression vectors with the fibwort mosaic virus (FMV) full length transcript (FLt) promoter containing single or double enhancer domains. (1997) Transgenic Research; vol. 6, pp. 143-156.*
Puddephat et al. Transformation of *Brassica oleracea* L.: a critical review. (1996) Molecular Breeding; vol. 2; pp. 185-210.*
Iwamoto et al., Evolutionary Relationship of Plant Catalase Genes Inferred From Exon-Intron Stuctures: Isozyme Divergence After The Separation of Monocots And Dicots, *Theor. Appl. Genet.*, 1998, vol. 97: No. 1-2, pp. 9-19.
Iwamoto et al., Differential Diurnal Expression of Rice Catalase Genes: The 5'-Flanking Region of *CatA* Is Not Sufficient For Circadian Control, *Plant Science*, 2000, vol. 151, No. 1, pp. 39-46.
English translation of "Research Result Information on Biological Resources (1999) 99-02" originally submitted with application upon filing.
Chen et al., "Differential Accumulation of Salicylic Acid and Salicylic Acid-Sensitive Catalase in Different Rice Tissues", *Plant Physiol.*, vol. 114, 1997, pp. 193-201.

* cited by examiner

*Primary Examiner*—Cathy Kingdon Worley
(74) *Attorney, Agent, or Firm*—Richard M. Klein; Fay Sharpe LLP

(57) ABSTRACT

The present invention provides a rice catalase B promoter for inducing expression specifically in at least one site of roots and stem apices. By using this promoter, it is possible to synthesize a resistance substance against nematodes or soil pathogens in roots; synthesize a substance promoting the development of roots in the roots; produce a gene recombinant plant in which expression of a selective marker in the redifferentiated plant body is limited to roots when the plant is young, so as to suppress the expression when the plant is matured; or the like. Further, the capability of expression in stem apices can be used to develop a technique for suppress gene expression in vigorously proliferating cells.

9 Claims, 5 Drawing Sheets

Leaf blade

Leaf sheath

Root (a)

```
      ↑-1066
ctgcaggtca acggatctta ttttccatt ataatatata taataaataa atatatgttt  -1007
acttttatta tagtactta aaagataaat ctatatatgt tgttctagtt cctttaaact  -947
aaatattatt aaagttatta atggttaaag ttataaaagt ttgatatcaa actcgtccaa  -887
aatgtcgatt aatatcgaac cggagcgagt acagtattag tagcaagtca gccacatggg  -827
acatggccca catgcatgca cgtcgtatga acacaccgtg attctttgcc acttgcataa  -767
tattctagca ctgctatact acacgacgac tgacggcgac gtcagttcag tttagtttgc  -707
cgcatccatc gcgaaggcta ctctacccat cccattttt tttaaaaaa aatactataa   -647
atctaaatat cttacattag atttgtatat tttaaagcaa agagaataat atgtagatat  -587
aagtatgtac ctactcgctc gagcacaaga tcactgcaac aagcattgaa gatcgctcct  -527
agcaatggtc tcaacttacc atgtaaacta agagcaacta taatgttttt ctttattag   -467
gaatggttgc atcttatatt ttgagattga gaaaacacat atagaaatta tacagagattt  -407
agcattggg atgccggccg gattcctgat ttccagtct ctggctttct ttttaaacaa    -347
aaacgaaaaa agcagtgatc cgatcgatca cgatgagcga gctagtaagc tccaaaacaa  -287
aatagagtac gtacgtataa tcctagagtc cggataataa tttggatcg gttcgcgtt    -227
aaaaaagtct tatctcctcg tgatcccttt tttgatcg atccatgttc gtagtacgtg    -167
acaagcacgc gcaccaaccg aagcaggtac ctgtgtcgct gcctgtgggc cccacacacc  -107
ccaagacggc cattaataaa caaacacgac gtgacgaag agaagggagg ccggcaagaa   -47
                                                              ↑
                                                            -1+1
gcatactagc acgctacgaa accccctta tcttcgtccc caaattgcac tacaaaaaag   14
gccgcccctt tcttctctcc tcgtccttat caccaccaat ccgatcctct tctcttctct   74
tctcttcttc cccacatcca gttcgattct catctctccc acaacaaatc acgccatgga  134
tccctacaag gtgccgcctt ttcctgattt tcttttcttc tagatcgatc gtcgatttgg  194
ttggttttgg tttcttgatg cgctcatccc aatctgactg actcactgga ttcctcctcc  254
ttgcagcatc ggccgtccag cggagcaat tcacccttct ggac                    298
                                                 ↑298
SEQ ID No. 1
```

RICE CATALASE B PROMOTER

TECHNICAL FIELD

The present invention relates to a promoter expressing a foreign gene introduced into a plant in roots and/or stem apices. More particularly, the present invention relates to a method for expressing a foreign gene in roots and/or stem apices using a part of the promoter region of the rice catalase gene B (hereinafter referred to as CatB).

BACKGROUND ART

Roots serve as support for preventing a plant from falling down, and more importantly, draw water and nutrients. A root branches to extend surface area so as to increase an area capable of absorption. The root also has a function of secreting and linking an organic acid, which makes a substance more absorbable, to phosphor, iron, or the like, and absorbing them. The root also has a function of synthesizing and secreting a substance like a lubricant so as to help the tip of the root grow in the soil. Synthesis and storage of plant hormones are also a role of the root. Further, the root stores energy obtained by photosynthesis, or stores phosphor during a juvenile stage and translocates it in the future. Plants, and especially roots, which cannot move as can animals suffer from a number of stresses from the surrounding environment, and take a number of measures against them.

These functions of roots are associated, for example in rice, with the following genes: cyclophyllin (Cyp) gene (Buchholz et al., Plant Mol. Biol. 25: 837-843 (1994)), lipid transfer protein (LTP) gene (Vignols et al., Gene 16: 265-270 (1994)), phenylalanine ammonia lyase (PAL-ZB8) gene (Zhu et al., Plant Mol. Biol. 29: 535-550 (1995)), histone H3 gene (Terada et al., Plant Mol. Biol. 27: 17-26 (1995)), basic chitinase (RC24) gene (Xu et al., Plant Mol. Biol. 30: 387-401 (1996)), caleosin gene (Naested et al., Plant Mol. Biol. 44: 463-476 (2000)), and the like, which are already known to be expressed in the root.

In some plants other than rice, the elongation factor eEF1A gene (Tremousaygue et al., Plant J 20:553-561(1999), myrosinase gene Pyk10 (Nitz et al., Plant Science 161: 337-346 (2001)), iron transporter (IRT2) gene (Vert et al., Plant J 26:181-189 (2001)), and the like of *Arabidopsis*; the glutathione S transferase (GST) gene (Klinedinst et al., Plant Mol Biol 42:679-688 (2000)), nitrate reductase (Hansch et al., J Exp Bot 52:1251-1258 (2001)) and the like of tobacco; or the pectinmethylesterase (Roger et al., Plant Science 160: 713-721(2001)) and the like of flax, are already known to be expressed in roots.

Shoot apex refers to the tip of a stem in a nutrition growth stage and its surrounding portions. In higher plants, stem apices have a capability of undergoing cell division to produce new cells. Examples of a gene expressed in stem apices include the lipid transfer protein (Itp1) gene (Canevascini et al., Plant Physiol., 112: 513-524 (1996)); homeobox (NTH15) gene (Tamaoki et al., Plant Cell Physiol., 38:917-927 (1997)), and gibberellin 3beta-hydroxylase gene (Itoh et al., Plant J., 20:15-24 (1999)) of tobacco (*Nicotiana tabacum*); and the pyrroline-5-carboxylate reductase gene (Hua et al., Plant Physiol., 114: 1215-1224 (1997)), ERECTA gene (Yokoyama et al., Plant J., 15:301-310 (1998)), ATML1 gene (Sessions et al., Plant J., 20:259-263 (1999)), and FAD3 gene (Matsuda et al., Planta, 213:833-840 (2001)) of *Arabidopsis*. These studies demonstrated that the tissue specificity of expression of these genes is regulated by their promoters.

Recently, a method of linking a promoter capable of expressing in roots with a gene capable of contributing to the development, disease resistance and stress resistance of a root and introducing the gene into plants has received attention as a promising biotechnology technique.

An attempt has been made to use a promoter for a viral gene in order to express a foreign gene in plants (e.g., MacFarlane and Popovich, Virology 267: 29-35 (2000); and Mazithulela et al., Plant Science 155: 21-29 (2000)). However, viruses spread after infection. Promoters derived from plant genes are superior to promoters derived from viral genes for the purpose of limiting the expression site of genes to a cellular level.

There are several known promoters for genes expressed in roots, which have been found in maizes and the like. Recombinant DNA technology can be used to confer disease resistance in roots. U.S. Pat. No. 6,284,948, entitled "Genes and methods for control of nematodes in plants", discloses an example of conferring nematode resistance in roots. Here, a nematode resistance gene is expressed using a plant ubiquitin gene promoter. However, this ubiquitin promoter has a low level of organ specificity and is constantly expressed.

An example of a root-specific promoter is disclosed in U.S. Pat. No. 6,271,437, entitled "Soybean gene promoters". Here, a method is described in which a promoter for a soybean cyst nematode gene is used to express a foreign gene in roots. Examples of a toot-specific promoter are disclosed in USP application 2001/0016954, entitled "Root specific promoters". These examples include a b1-tubulin gene promoter derived from *Arabidopsis*, a ribosome protein RPL16A gene promoter, an ARSK1 gene promoter, and a soybean metallothionein-like gene promoter. It is described that these promoters were used to confer nematode resistance.

These promoters have the following problems: the activity of the promoters is generally insufficient to provide a practical application; the promoters do not function in monocotyledons, including cereals such as rice and the like; their organ specificity is low; or the like.

Therefore, if a number of promoters acting in various development stages of cereals are isolated, the features of these promoters are revealed, and promoter cassettes having different tissue specificities and high activity are produced, then such promoter cassettes are very useful for breeding crops, such as rice and the like.

PROBLEMS TO BE SOLVED BY THE INVENTION

An object of the present invention is to provide a plant promoter having a high level of activity in roots and/or stem apices. More specifically, the object of the present invention is to provide a practical promoter which overcomes problems with the activity of conventional promoters (i.e., the activity is generally insufficient for practical applications; the activity is not exhibited in monocotyledons, such as rice and the like; the organ specificity of the activity is low; or the like).

DISCLOSURE OF THE INVENTION

Means for Solving the Problems

The present invention was completed based on a finding that a part of the base sequence of the promoter region of the rice catalase B (CatB) gene can be used to express a foreign gene in roots.

The present invention provides the following.

1. A promoter, comprising a sequence of at least 10 contiguous nucleotides of a sequence indicated by SEQ ID No. 1, wherein the promoter has substantially the same promoter activity as or greater than that of the sequence indicated by SEQ ID No. 1.

2. A promoter according to item 1, wherein the promoter comprises a sequence of at least 10 contiguous nucleotides of a sequence indicated by SEQ ID No. 11, and the promoter has substantially the same promoter activity as or greater than that of the sequence indicated by SEQ ID No. 1.

3. A promoter according to item 1, wherein the promoter comprises a sequence of at least 10 contiguous nucleotides of a sequence indicated by SEQ ID No. 12, and the promoter has substantially the same promoter activity as or greater than that of the sequence indicated by SEQ ID No. 1.

4. A composition for expressing a desired gene in at least one site of roots and stem apices, in plants, the composition comprising:
 1) a promoter comprising a sequence of at least 10 contiguous nucleotides of a sequence indicated by SEQ ID No. 1, and the promoter has substantially the same promoter activity as or greater than that of the sequence indicated by SEQ ID No. 1; and
 2) the desired gene.

5. A composition according to item 4, wherein the promoter comprises a sequence of at least 10 contiguous nucleotides of a sequence indicated by SEQ ID No. 11, and the promoter has substantially the same promoter activity as or greater than that of the sequence indicated by SEQ ID No. 1.

6. A composition according to item 4, wherein the promoter comprises a sequence of at least 10 contiguous nucleotides of a sequence indicated by SEQ ID No. 12, and the promoter has substantially the same promoter activity as or greater than that of the sequence indicated by SEQ ID No. 1.

7. A composition according to item 4, wherein the plant is a monocotyledon or a dicotyledon.

8. A composition according to item 4, wherein the plant is a monocotyledon.

9. A composition according to item 4, wherein the plant is rice, *Arabidopsis*, maize, wheat, barley, tomato, cucumber, eggplant, potato, lettuce, Japanese radish, or carrot.

10. A composition according to item 4, wherein the desired gene is a gene encoding at least one polypeptide selected from the group consisting of a polypeptide capable of conferring resistance, a peptide capable of promoting development of roots, and a selective marker for a redifferentiated plant body.

11. A composition according to item 4, wherein the at least one site of roots and stem apices includes a tip portion of the roots.

12. A composition according to item 4, wherein the at least one site of roots and stem apices includes a meristem region of a young monocotyledon plant.

13. A composition according to item 4, wherein the at least one site of roots and stem apices includes a stem apex portion.

14. A plant expression cassette for expressing a desired gene in at least one site of roots and stem apices in plants, the plant expression cassette comprising:
 1) a promoter comprising a sequence of at least 10 contiguous nucleotides of a sequence indicated by SEQ ID No. 1, and the promoter has substantially the same promoter activity as or greater than that of the sequence indicated by SEQ ID No. 1; and
 2) the desired gene.

15. A plasmid for expressing a desired gene in at least one site of roots and stem apices in plants, the plasmid comprising:
 1) a promoter comprising a sequence of at least 10 contiguous nucleotides of a sequence indicated by SEQ ID No. 1, and the promoter has substantially the same promoter activity as or greater than that of the sequence indicated by SEQ ID No. 1; and
 2) the desired gene,
 wherein the promoter is operably linked to the desired gene.

16. A plant cell adapted to express a desired gene in at least one site of roots and stem apices in plants, the plant cell comprising:
 1) a promoter comprising a sequence of at least 10 contiguous nucleotides of a sequence indicated by SEQ ID No. 1, and the promoter has substantially the same promoter activity as or greater than that of the sequence indicated by SEQ ID No. 1; and
 2) the desired gene.

17. A plant tissue adapted to express a desired gene in at least one site of roots and stem apices in plants, the plant tissue comprising:
 1) a promoter comprising a sequence of at least 10 contiguous nucleotides of a sequence indicated by SEQ ID No. 1, and the promoter has substantially the same promoter activity as or greater than that of the sequence indicated by SEQ ID No. 1; and
 2) the desired gene.

18. A transgenic plant adapted to express a desired gene in at least one site of roots and stem apices in plants, the transgenic plant comprising:
 1) a promoter comprising a sequence of at least 10 contiguous nucleotides of a sequence indicated by SEQ ID No. 1, and the promoter has substantially the same promoter activity as or greater than that of the sequence indicated by SEQ ID No. 1; and
 2) the desired gene.

19. A plant seed adapted to express a desired gene in at least one site of roots and stem apices in plants, the plant seed comprising:
 1) a promoter comprising a sequence of at least 10 contiguous nucleotides of a sequence indicated by SEQ ID No. 1, and the promoter has substantially the same promoter activity as or greater than that of the sequence indicated by SEQ ID No. 1; and
 2) the desired gene.

20. A method for expressing a desired gene in at least one site of roots and stem apices in plants, the method comprising:
 1) providing the plants with a nucleic acid encoding a promoter comprising a sequence of at least 10 contiguous nucleotides of a sequence indicated by SEQ ID No. 1, and the promoter has substantially the same promoter activity as or greater than that of the sequence indicated by SEQ ID No. 1:
 2) providing the plants with a nucleic acid encoding the desired gene; and
 3) placing the plants under conditions which permit the promoter to operate.

21. A gene product obtained by a method for expressing a desired gene in at least one site of roots and stem apices in plants, the method comprising:
 1) providing the plants with a nucleic acid encoding a promoter comprising a sequence of at least 10 contiguous nucleotides of a sequence indicated by SEQ ID No. 1, and the promoter has substantially the same promoter activity as or greater than that of the sequence indicated by SEQ ID No. 1;
 2) providing the plants with a nucleic acid encoding the desired gene; and
 3) placing the plants under conditions which permit the promoter to operate.

22. A method for producing a plant adapted to express a desired gene in at least one site of roots and stem apices, the method comprising:

1) providing a plasmid containing a promoter comprising a sequence of at least 10 contiguous nucleotides of a sequence indicated by SEQ ID No. 1, and the promoter has substantially the same promoter activity as or greater than that of the sequence indicated by SEQ ID No. 1;

2) transforming a plant cell with the plasmid; and 3) culturing the transformed plant cell.

Items 14 to 22 may be specified by the features of items 5 to 13.

BRIEF DESCRIPTION OF THE DRAWINGS

FIG. 5 shows the CatB promoter region of SEQ ID No. 1.

DETAILED DESCRIPTION OF THE INVENTION

Figure 1:
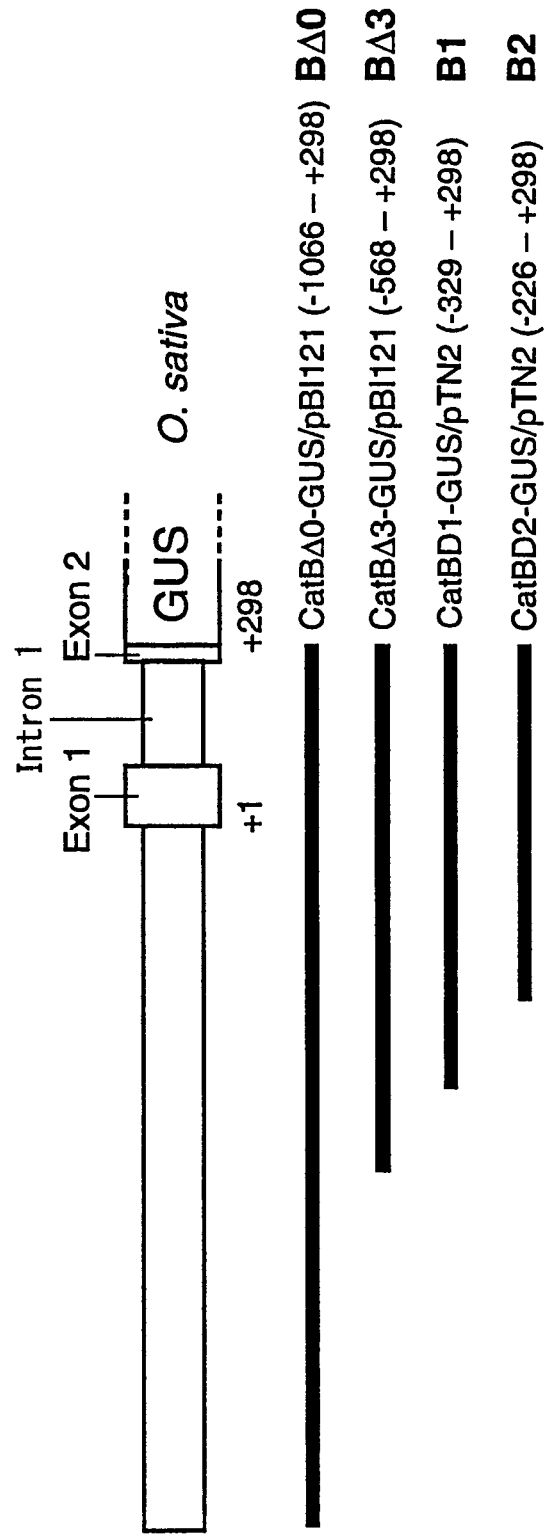
FIG. 1 shows various DNA constructs used in experiments.

It should be understood throughout the present specification that articles for singular forms (e.g., "a", "an", "the", etc. in English; "ein", "der", "das", "die", etc. and their inflections in German; "un", "une", "le", "la", etc. in French; and articles, adjectives, etc. in other languages) include the concept of their plurality unless otherwise mentioned. It should be also understood that terms as used herein have definitions ordinarily used in the art unless otherwise mentioned.

(Description of Sequences)

SEQ ID No. 1 indicates the nucleic acid sequence of a CatB promoter region (1364 bp) (−1066 to +298 where the starting point of cDNA is regarded as +1; see FIG. 5).

SEQ ID No. 2 indicates the nucleic acid sequence of the CatB gene (4985 bp).

SEQ ID No. 3 indicates a BΔ3 fragment (866 bp).

SEQ ID No. 4 indicates a B1 fragment (627 bp). At positions 1 to 6, AAAAAA in the base sequence of the CatB catalase gene is changed to AAGCTT, which is a HindIII cleavage site. At position 460, T is replaced with C, thereby destroying the translation start codon of the CatB catalase gene.

SEQ ID No. 5 indicates a B2 fragment (524 bp). At positions 1 to 6, AAAAAA in the base sequence of the CatB catalase gene is changed to AAGCTT, which is a HindIII cleavage site. At position 357, T is replaced with C, thereby destroying the translation start codon of the CatB catalase gene.

SEQ ID No. 6 is a sequence corresponding to 102-131 of the CatB cDNA.

SEQ ID No. 7 is a sequence corresponding to 484-455 of the CatB cDNA.

SEQ ID No. 8 is a primer 3D3-F1 used herein in one embodiment.

SEQ ID No. 9 is a primer 3D3-F2 used herein in one embodiment.

SEQ ID No. 10 is a primer BD3-MR used herein in one embodiment.

SEQ ID No. 11 indicates a promoter region of −329 to +298.

SEQ ID No. 12 indicates a promoter region of −329 to −227.

(Definition of Terms)

"Promoter" as used herein refers to a genetic element or factor to which RNA polymerase binds to initiate transcription. "Promoter region" as used herein refers to a region having promoter activity in the vicinity of a certain structural gene sequence. A promoter region is specified by a base sequence upstream of a normal gene, to which RNA polymerase binds when the transcription of the gene is initiated. "Promoter activity" as used herein, processed by a certain factor, refers to activity in which transcription is initiated by the factor acting on RNA polymerase or the like.

"Plant" as used herein includes any of the monocotyledons and dicotyledons. Examples of preferable plants include monocotyledons belonging to the family rice, such as wheat, maize, rice, barley, sorghum, and the like. Other examples of preferable plants include tobacco, pimento, eggplant, melon, tomato, sweet potato, cabbage, onion, broccoli, carrot, cucumber, citrus, Chinese cabbage, lettuce, peach, potato, and apple. Preferable plants are not limited to crops, but include flowers, trees, grasses, weeds, and the like. Plant means whole plants, plant organs, plant tissues, plant cells, and seeds unless otherwise specified. Examples of plant organs include roots, leaves, stems, flowers, and the like. Examples of plant cells include callus and suspension cultured cells.

"At least one site of roots and stem apices" as used herein refers to at least one site selected from the site group consisting of roots and stem apices. Therefore, "at least one site of roots and stem apices" includes a part of a root or a part of a stem apex. "at least one site of roots and stem apices" also includes meristems.

"Meristem" as used herein refers to plant cambium comprising differentiated cells and a site capable of differentiating into other dividing cells or particular types of cells. Meristems are often observed in a growing portion. Examples of meristems include growth points, stem apices (shoot apices), root apices or tips, root apical meristems, apical meristems, and the like.

"Root" as used herein refers to organs which exist underground, serve as support, and draw water. The tip is called a root cap whose internal portions are surrounded by the epidermis and called central cylinder. Vessels and sieve tubes run in a central cylinder. A root hair, which is a projecting part of an epidermis cell, is present slightly down the tip of a root. Epidermis cells in or around a root hair vigorously draw water. The life of a root hair is from several days to several weeks during which the root constantly elongates so that the position of the root hair is moved forward. A whole root is also herein called a root system. For example, in a seminal root of rice, about 5 to 20 adventitious roots grow from each node of a single coleoptile and above. Roots growing from a node are called crown root. A greater number of roots grow from an upper node. First and second branched roots grow from an upper node. Roots may grow to a length of about 1 m at maximum. Roots contain meristems.

"Stem apex" as used herein is also called a shoot apex and refers to a root apical meristem of a stem and surrounding sites. The stem apex includes the vegetative stem apex which forms stems and laterally leaves and the reproductive stem apex which forms an inflorescence or flower. The stem apex contains a meristem. The stem apex refers to the tip of a stem and its surrounding portions in the vegetative phase. The stem apex of a higher plant is capable of dividing into new cells.

"Catalase" as used herein refers to an enzyme capable of catalyzing a reaction which decomposes peroxide (EC1.11.1.6). Catalases may oxidize $C_2H_5OH$, $CH_3OH$, $CH_3COOH$, $HCOOH$, $HNO_2$, and the like in the presence of $H_2O_2$, $CH_3OOH$, and $C_2H_5OOH$. The catalase is present in any aerobic cells no matter whether they are of animals, plants, or microorganisms. In animals, liver, kidney, and erythrocytes contain a large amount of the catalase. A bovine liver catalase has a molecular weight of about 230,000. One molecule of this enzyme contains 4 protohematins as functional groups. In plants, the catalase includes catalase B isolated by the present inventors.

"Fragment" of a nucleic acid molecule as used herein refers to a polynucleotide having a length which is shorter than the full length of reference DNA but sufficient for use at least as a probe or a primer. A certain DNA fragment has to be specifically hybridizable in order to be used as a selective probe or a selective primer for a nucleic acid molecule from which the fragment originated. "A certain DNA hybridizes specifically to" as used herein indicates that a provided nucleic acid molecule can be separately detected or amplified by its DNA fragment. The selective probe may have a length of representatively at least 10 nucleotides, preferably at least 15 nucleotides, more preferably at least 20 nucleotides, and even more preferably at least 30, 40 or 50 nucleotides, and may further have a length of more than 50 nucleotides. The selective probe may be available as a product of PCR amplification using a selective primer. When a selective primer is used as at least one of a pair of primers in PCR, the selective primer has a length of representatively at least 9 nucleotides, preferably at least 10 nucleotides, more preferably at least 15 nucleotides, even more preferably at least 17, 18, 19, 20, 21, 22, 23, 24, 25, 30 or 50 nucleotides, or more than 50.

"Homolog" of a nucleic acid molecule as used herein refers to a nucleic acid molecule having a nucleotide sequence which is homologous to the nucleotide sequence of a reference DNA. Representatively, homolog refers to a polynucleotide which hybridizes to a reference nucleic acid molecule under stringent conditions. In the case of a promoter of the present invention, a "homolog" of the promoter refers to a nucleic acid molecule which has a nucleic acid sequence sharing homology with the promoter sequence, and has the same or similar expression characteristics (e.g., site specificity, period specificity, responsiveness to stresses, and the like).

As used herein, "homology" of a gene refers to the magnitude of identity between two or more gene sequences. Therefore, the greater the homology between two genes, the greater the identity between their sequences. Whether or not two genes have homology is determined by comparing their sequences directly or by a hybridization method under stringent conditions. When two gene sequences are directly compared with each other, the genes have homology if the sequences of the genes have representatively at least 50%, preferably at least 70%, more preferably at least 80%, 90%, 95%, 96%, 97%, 98%, or 99% identity to each other.

The magnitude of homology is herein determined by a sequence analyzing tool, BLAST, using its default parameters.

Therefore, nucleic acid molecules containing a sequence of at least 10 contiguous nucleotides contained in the promoter sequence of the present invention may have the same or similar activity as the promoter of the present invention. Such activity can be confirmed by an assay using a beta-glucuronidase (GUS) gene, a luciferase gene, or a GFP gene as a reporter gene, or a biological or cellular histological test. Such an assay is a well known technique common used in the art (Maliga et al., Methods in Plant Molecular Biology: A laboratory course. Cold Spring Harbor Laboratory Press (1995); Jefferson, Plant Molec. Biol. Reporter 5: 387 (1987); Ow et al., Science 234: 856 (1986); Sheen et al., Plant J. 8: 777-784 (1995)). Therefore, it is possible for those skilled in the art to, without any difficulty, confirm that a nucleic acid molecule containing a sequence of at least 10 contiguous nucleotides contained in the promoter sequence of the present invention has the same or similar activity as, or activity substantially higher than or equal to, that of the promoter of the present invention. Promoter activity is herein said to be substantially higher or equal to that of the promoter of the present invention when it is confirmed by the above-described assay within a detection error.

The length of the promoter of the present invention is usually at least 10 nucleotides, and may be preferably at least 20 nucleotides, at least 30 nucleotides, at least 40 nucleotides, at least 50 nucleotides, at least 60 nucleotides, at least 70 nucleotides, at least 80 nucleotides, at least 90 nucleotides, at least 100 nucleotides, at least 150 nucleotides, at least 200 nucleotides, and at least 300 nucleotides.

The promoter of the present invention linked to a conventional promoter (e.g., a minimum promoter (a promoter containing about 80 base pairs derived from 35S promoter (Hatton et al., Plant J., 7:859-876 (1995); Rouster et al., Plant J., 15: 435-440 (1998); Washida et al., Plant Mol. Biol., 40:1-12 (1999)); etc.) can be used. In this case, if a promoter, which originally has no or weak tissue specificity, or which has another type of specificity, is linked with the promoter or its fragment of the present invention, the resultant promoter can function tissue specifically in roots and/or stem apices (Hatton et al., Plant J., 7:859-876 (1995); Rouster et al., Plant J., 15: 435-440 (1998); Washida et al., Plant Mol. Biol., 40:1-12 (1999)).

The promoter of the present invention may be used to modify monocotyledonous as well as dicotyledonous plants and other organisms. This is because both plants have a similar mechanism for regulating transcription. For example, it has been reported that the zein gene promoter of maize was expressed with the same tissue characteristic in tobacco (Schernthaner et al., EMBO J., 7:1249-1255 (1988)); and the glutelin gene promoter of rice was expressed with the same tissue characteristic in tobacco (Leisy et al., Plant Mol. Biol., 14: 41-50 (1989)). Particularly preferable subject plants include in addition to rice, wheat, maize, barley, sorghum, citrus, Chinese cabbage, lettuce, tobacco, peach, potato, tomato, and apple.

When a gene is herein discussed, "vector" refers to a vector capable of introducing a polynucleotide sequence of interest into a target cell. Such a vector includes a vector containing a promoter capable of self-replication in prokaryotic cells, yeast, animal cells, plant cells, insect cells, individual animals or being incorporated into the chromosome thereof, and positioned at a site suitable for the transcription of a polynucleotide of the present invention. "Recombinant vector" for plant cells includes Ti plasmid, a tobacco mosaic virus vector, and the like.

Examples of a vector introducing method include any method of introducing DNA into plant cells, for example, transfection, transduction, and transformation using the following: *Agrobacterium* (Japanese Laid-Open Publication No. 59-140885, Japanese Laid-Open Publication No. 60-70080, and WO94/00977), an electroporation method (Japanese Laid-Open Publication No. 60-251887), a particle gun (gene gun) method (Japanese Patent No. 2606856 and Japanese Patent No. 2517813), or the like.

"Detection or qualification" of expression of the promoter of the present invention may be achieved using an appropriate method including, for example, mRNA measurement and immunological measurement methods. Molecular biological measurement methods include, for example, a northern blot method, a dot blot method, a PCR method, and the like. Immunological measurement methods include, for example, an ELISA method, an RIA method, a fluorescent antibody method, a western blot method, an immunohistological staining method, and the like using a microtiter plate. Quantitation methods include an ELISA method, an RIA method, and the like.

"Expression level" refers to of the level of a protein or mRNA of the present invention expressed in a target cell or the like. Such an expression level includes the protein level of the polypeptide of the present invention evaluated by any appropriate method including immunological measurement methods, such as an ELISA method, an RIA method, a fluorescent antibody method, a western blot method, an immunohistological staining method, and the like, using an antibody of the present invention; or the mRNA level of the polypeptide of the present invention evaluated by any appropriate method including biological measurement methods including a northern blot method, a dot blot method, a PCR method, and the like. "Change in an expression level" refers to an increase or decrease in an expression level determined by the protein or mRNA level of the peptide of the present invention evaluated by any appropriate method including the above-described immunological or biological measurement methods. By observing the absolute or relative value of the expression level, it is possible to determine whether or not a certain promoter acts specifically.

"Transformant" refers to the whole or a part of an organism, such as a cell or the like, produced by transformation. Examples of the transformant include prokaryotic cells, yeast, animal cells, plant cells, insect cells, and the like. The transformant is also called a transformed cell, transformed tissue, a transformed host, or the like, depending on what is transformed.

"Gene" as expressed herein has a meaning common in the art and refers to a factor which determines a genetic trait. Desired genes to be expressed by the method of the present invention are any gene which is desired to be specifically expressed by the method of the present invention, including polypeptides capable of conferring resistance against nematodes, soil pathogens, or the like, polypeptides capable of accelerating the development of roots, selective markers for redifferentiated plant bodies, and the like.

"Redifferentiation" as used herein refers to a phenomenon that a whole entity is reconstructed from a part of an entity. For example, a plant body is formed from a piece of tissue, such as a cell, a leaf, a root, or the like.

A method of redifferentiating a transformant to a plant body is well known in the art. Such a method is illustrated in Rogers et al., Methods in Enzymology 118: 627-640 (1986); Tabata et al., Plant Cell Physiol., 28: 73-82 (1987); Shaw, Plant Molecular Biology: A practical approach. IRL press (1988); Shimamoto et al., Nature 338: 274 (1989); Maliga et al., Methods in Plant Molecular Biology: A laboratory course. Cold Spring Harbor Laboratory Press (1995); and the like. Therefore, it is possible for those skilled in the art to use the above-described well-known method, depending on a transgenic plant of interest, so as to carry out redifferentiation.

The presence of a desired, modified property of a redifferentiated transformant may be confirmed by performing an appropriate assay depending on the type of the property. For example, the GUS gene as a reporter gene is fused with a promoter which is in turn introduced into a plant body to produce a transformant. The transformation can be confirmed by detecting GUS activity by histological staining. In this case, a GFP gene or a luciferase gene, which are fluorescent proteins, can be used as a reporter gene. Any of these genes are used in assays for various promoters. The details of the genes will be described in the examples below. When it is intended to confer resistance against pathogenic bacteria (stress resistance), a model bacterium (e.g., *Pseudomonas syringae* pv. tabaci) is inoculated into a redifferentiated plant body. In this case, a property change in the redifferentiated plant body may be evaluated by observing the presence or absence of the change by comparing it with a control plant.

Plants can be herein cultivated by any known method in the art. Methods of cultivating plants are illustrated in, for example, "Moderu-shokubutsu-no-Jikken-Purotokoru For Ine Shiroinunazuna: Saibo-kogaku Bessatsu-shokubutsu-saibo-kogaku sirizu 4; Ine-no-saibaiho [Experimental Protocol for Model Plants For Rice and "*Arabidopsis thaliana*: Cellular Engineering, Special Issue, Plant Cellular Engineering Series 4; Rice Cultivating Methods]" (Kazutoshi Okuno) pp. 28-32, and "Arabidopushisu-no-saibaiho [Cultivating Methods for *Arabidopsis*]" (Yasuo Tanba) pp. 33-40 (Supervised by Ko Shimamoto and Kiyotaka Okada), which are not herein described in detail. For example, *Arabidopsis thaliana* can be cultivated by any of soil culture, rock wool culture, and water culture. After dissemination, flowering is first observed in about 4 weeks if the plant is cultivated under constant light of a white color fluorescent lamp (about 6000 lux). After flowering, seeds are fully matured in about 16 days. 40 to 50 seeds are obtained from one pod. During 2 to 3 months from dissemination to death, about 10,000 seeds are obtained. The dormancy term of the seed is short. Full-matured seeds after about one week drying are germinated 2 to 3 days after absorbing water. Note that if the seeds are subjected to cryogenic processing at 4° C. for 2 to 4 days after water absorption and dissemination, the seeds are simultaneously germinated.

Best Mode for Carrying Out the Invention

According to one aspect, the present invention relates to a promoter comprising a sequence of at least 10 contiguous nucleotides of a sequence indicated by SEQ ID No. 1. The promoter may have substantially the same promoter activity as or greater than that of the sequence indicated by SEQ ID No. 1. Preferably, the promoter may comprise a sequence of at least 10 contiguous nucleotides of a sequence indicated by SEQ ID No. 11.

More preferably, the present invention provides a nucleic acid molecule comprising a sequence of at least 10 contiguous nucleotides of a sequence indicated by SEQ ID No. 12. The promoter may have substantially the same promoter activity as or greater than that of the sequence indicated by SEQ ID No. 1. This nucleic acid molecule has promoter activity to specifically promote expression in roots including meristems. To the knowledge of the present inventors, such a sequence capable of conferring promoter activity was not previously found in particularly rice and *Arabidopsis*, and therefore, the present invention can be said to achieve an advantageous effect in the art.

The above-described specific sequence range only indicates one preferable sequence range in the present invention. The present invention is not so limited. Therefore, the present invention can be specified as another appropriate region selected by those skilled in the art in accordance with methods as described herein. Such selection methods can be carried out without undue experimentation by referencing commonly used techniques well known in the art.

In another aspect, the present invention provides a composition for expressing a gene in at least one site of roots and stem apices in plants. The composition comprising:

1) a promoter comprising a sequence of at least 10 contiguous nucleotides of a sequence indicated by SEQ ID No. 1, and, the promoter has substantially the same promoter activity as or greater than that of the sequence indicated by SEQ ID No. 1; and 2) the desired gene.

As described above, the promoter 1) promotes expression specific to at least one site of roots and stem apices. Therefore, such a composition provides a system capable of specifically expressing in at least one site of roots and stem apices, i.e, advantageous usefulness in the art.

In one embodiment, the promoter may comprise a sequence of at least 10 contiguous nucleotides of a sequence indicated by SEQ ID No. 11, and the promoter has substantially the same promoter activity as or greater than that of the sequence indicated by SEQ ID No. 1.

In another embodiment, the promoter may comprise a sequence of at least 10 contiguous nucleotides of a sequence indicated by SEQ ID No. 12, and the promoter has substantially the same promoter activity as or greater than that of the sequence indicated by SEQ ID No. 1. In another embodiment, the plant may be a monocotyledon or a dicotyledon. The organism is not limited to monocotyledons or dicotyledons. Therefore, the promoter of the present invention may be derived from organisms other than plants, such as animals or the like, or plants other than monocotyledons and dicotyledons, as long as the promoter has the same effect. In a preferred embodiment, the plant may be a monocotyledon. More preferably, the plant may be rice, *Arabidopsis*, maize, wheat, barley, tomato, cucumber, eggplant, potato, lettuce, Japanese radish, or carrot.

In another preferred embodiment, the length of the promoter of the present invention may be at least 20 nucleotides, at least 30 nucleotides, at least 40 nucleotides, at least 50 nucleotides, at least 60 nucleotides, at least 70 nucleotides, at least 80 nucleotides, at least 90 nucleotides, at least 100 nucleotides, at least 150 nucleotides, at least 200 nucleotides, or at least 300 nucleotides.

In another embodiment, the promoter of the present invention may be linked with another promoter. In this case, by linking a promoter, which originally has no or weak tissue specificity, or which has another type of specificity, with the promoter or its fragment of the present invention, it is possible to produce a promoter which can function tissue specifically in at least one site of roots and/or stem apices.

In another embodiment, the desired gene may be a gene encoding at least one polypeptide selected from the group consisting of a polypeptide capable of conferring resistance to, for example nematodes or soil pathogens, a peptide capable of promoting development of roots, and a selective marker for a redifferentiated plant body.

In another embodiment, the at least one site of roots and stem apices may include a tip portion of roots. In another embodiment, the at least one site of roots and stem apices may include a stem apex portion. The at least one site of roots and stem apices may include meristems of young monocotyledon plants (e.g., rice). By promoting expression only in young plants, it is possible to produce crops (e.g., rice) in which the product of the introduced gene is not expressed or left.

In another aspect, the present invention provides a plant expression cassette for expressing a desired gene in at least one site of roots and stem apices in plants. The plant expression cassette may comprise:

1) a promoter comprising a sequence of at least 10 contiguous nucleotides of a sequence indicated by SEQ ID No. 1, and the promoter has substantially the same promoter activity as or greater than that of the sequence indicated by SEQ ID No. 1; and 2) the desired gene.

The plant expression cassette can be produced by techniques well known in the art. Such production techniques are herein exemplified in examples.

In another aspect, the present invention provides a plasmid for expressing a desired gene in at least one site of roots and stem apices in plants. The plasmid may comprise:

1) a promoter comprising a sequence of at least 10 contiguous nucleotides of a sequence indicated by SEQ ID No. 1, and the promoter has substantially the same promoter activity as or greater than that of the sequence indicated by SEQ ID No. 1; and 2) the desired gene.

The promoter is operably linked to the desired gene. The plasmid (or a vector) can be produced by techniques well known in the art. Such production techniques are herein exemplified in examples.

In another aspect, the present invention provides a plant cell adapted to express a desired gene in at least one site of roots and stem apices in plants. The plant cell may comprise:

1) a promoter comprising a sequence of at least 10 contiguous nucleotides of a sequence indicated by SEQ ID No. 1, and the promoter has substantially the same promoter activity as or greater than that of the sequence indicated by SEQ ID No. 1; and 2) the desired gene.

Such a plant cell can be produced by techniques well known in the art. For example, such a plant cell can be produced by transformation, transfection, or transduction using the plasmid of the present invention. Such methods are specifically exemplified herein and illustrated in examples.

In another aspect, the present invention provides a plant tissue adapted to express a desired gene in at least one site of roots and stem apices in plants. The plant tissue may comprise:

1) a promoter comprising a sequence of at least 10 contiguous nucleotides of a sequence indicated by SEQ ID No. 1, and the promoter has substantially the same promoter activity as or greater than that of the sequence indicated by SEQ ID No. 1; and 2) the desired gene.

The plant tissue can be produced by causing the plant cell of the present invention to redifferentiate, for example. Alternatively, it is possible to produce the plant tissue by injecting the composition of the present invention directly into plant tissue. Such a technique is well known in the art.

In another aspect, the present invention provides A transgenic plant adapted to express a desired gene in at least one site of roots and stem apices in plants. The transgenic plant may comprise:

1) a promoter comprising a sequence of at least 10 contiguous nucleotides of a sequence indicated by SEQ ID No. 1, and the promoter has substantially the same promoter activity as or greater than that of the sequence indicated by SEQ ID No. 1; and 2) the desired gene.

The plant tissue can be produced by causing the plant cell of the present invention to redifferentiate, for example. Such a technique is well known in the art, including, for example: for dicotyledons (e.g., tobacco, *Arabidopsis*, or the like), Rogers et al., Methods in Enzymology 118: 627-640 (1986); Tabata et al., Plant Cell Physiol., 28: 73-82 (1987); Shaw, Plant Molecular Biology: A practical approach. IRL press (1988); Maliga et al., Methods in Plant Molecular Biology: A laboratory course. Cold Spring Harbor Laboratory Press (1995); for rice, Shimamoto et al., Nature 338: 274 (1989); Hiei et al., Plant J. 6:271-282 (1994); Toki, Plant Mol. Biol. Rep. 15:16-21 (1997); and the like.

In another aspect, the present invention provides a plant seed adapted to express a desired gene in at least one site of roots and stem apices in plants. The plant seed may comprise:

1) a promoter comprising a sequence of at least 10 contiguous nucleotides of a sequence indicated by SEQ ID No. 1, and the promoter has substantially the same promoter activity as or greater than that of the sequence indicated by SEQ ID No. 1; and 2) the desired gene.

Such a plant seed can be produced by redifferentiating the above-described while keeping its fertility. Such a redifferentiation technique is well known in the art, including, for example: for dicotyledons (e.g., tobacco, *Arabidopsis*, and the like), Rogers et al., Methods in Enzymology 118: 627-640 (1986); Tabata et al., Plant Cell Physiol., 28: 73-82 (1987); Shaw, Plant Molecular Biology: A practical approach. IRL press (1988); Maliga et al., Methods in Plant Molecular Biology: A laboratory course. Cold Spring Harbor Laboratory Press (1995); for rice, Shimamoto et al., Nature 338: 274 (1989); Hiei et al., Plant J. 6:271-282 (1994); Toki, Plant Mol. Biol. Rep. 15:16-21 (1997).

In another aspect, the present invention provides a method for expressing a desired gene in at least one site of roots and stem apices in plants. The method may comprise:

1) providing the plants with a nucleic acid encoding a promoter comprising a sequence of at least 10 contiguous nucleotides of a sequence indicated by SEQ ID No. 1, and the promoter has substantially the same promoter activity as or greater than that of the sequence indicated by SEQ ID No. 1;

2) providing the plants with a nucleic acid encoding the desired gene; and 3) placing the plants under conditions which permit the promoter to operate.

Such a method can be carried out with commonly used techniques well known in the art if the promoter of the present invention is specified. Such an expression method is herein described above.

In another aspect, the present invention provides a gene product obtained by a method for expressing a desired gene in at least one site of roots and stem apices in plants. The method may comprise:

1) providing the plants with a nucleic acid encoding a promoter comprising a sequence of at least 10 contiguous nucleotides of a sequence indicated by SEQ ID No. 1, and the promoter has substantially the same promoter activity as or greater than that of the sequence indicated by SEQ ID No. 1;

2) providing the plants with a nucleic acid encoding the desired gene; and 3) placing the plants under conditions which permit the promoter to operate.

The at least one site of roots and stem apices is vigorously proliferating tissue. With this method, a large volume of the desired gene can be obtained.

In another aspect, the present invention provides a method for producing a plant adapted to express a desired gene in at least one site of roots and stem apices. The method may comprise:

1) providing a plasmid containing a promoter comprising a sequence of at least 10 contiguous nucleotides of a sequence indicated by SEQ ID No. 1, and the promoter has substantially the same promoter activity as or greater than that of the sequence indicated by SEQ ID No. 1;

2) transforming a plant cell with the plasmid; and 3) culturing the transformed plant cell.

A method for providing a plasmid, a transformation method, and a culture method are well known in the art, and are already described herein.

The present inventors have already isolated and analyzed the structure of the rice catalase CatB gene (DDBJ registration number: D64013 (SEQ ID No. 2)). Further, the 5'-upstream promoter region (−1066 to +298: this DNA fragment is herein called BΔ0, where the cDNA starting point is regarded as +1 (SEQ ID No. 1)) was fused with a reporter gene (beta-glucuronidase (GUS)). This combination was introduced into protoplasts prepared from a rice culture cell line (Oc cell) using electroporation so as to use GUS enzyme activity due to temporary gene expression as an indicator for measurement of the promoter activity. As a result, it was found that it had activity about 20.times greater than that of the cauliflower mosaic virus (CaMV) 35S promoter which is commonly used for introduction of a gene into plants. Accordingly, it was revealed that the promoter can be used to produce a promoter cassette for expressing a useful gene, and the present invention was completed and filed as a patent application (Japanese Patent No. 2955644 entitled "Rice CatB gene promoters").

Further, by northern hybridization analysis, the present inventors revealed that whereas CatB is strongly expressed in roots of a young rice plant, it is not expressed in the matured individual; and it is not strongly expressed in leaves, stems, and flowers (Iwamoto et al. Plant Science 151:39-46(2000)) (Table 1).

TABLE 1

Summary of Organ specificity of Rice Catalase Gene Expression (Major Expression Site)

| Gene Name | Expression Organ of Young Shoot Rice | Expression Organ of Flowering-stage Rice |
| --- | --- | --- |
| CatA | Leaf sheath | Anther |
| CatB | Root | (—) |
| CatC | Leaf blade | Leaf blade |

(Summary of northern analysis data announced by Iwamoto et al., Plant Science 151: 39-46 (2000), and data obtained thereafter)

Based on the above-described results, it was herein attempted to identify a portion of the CatB gene promoter region (Japanese Registration No. 2955644) which controls organ specificity.

Figure 2:
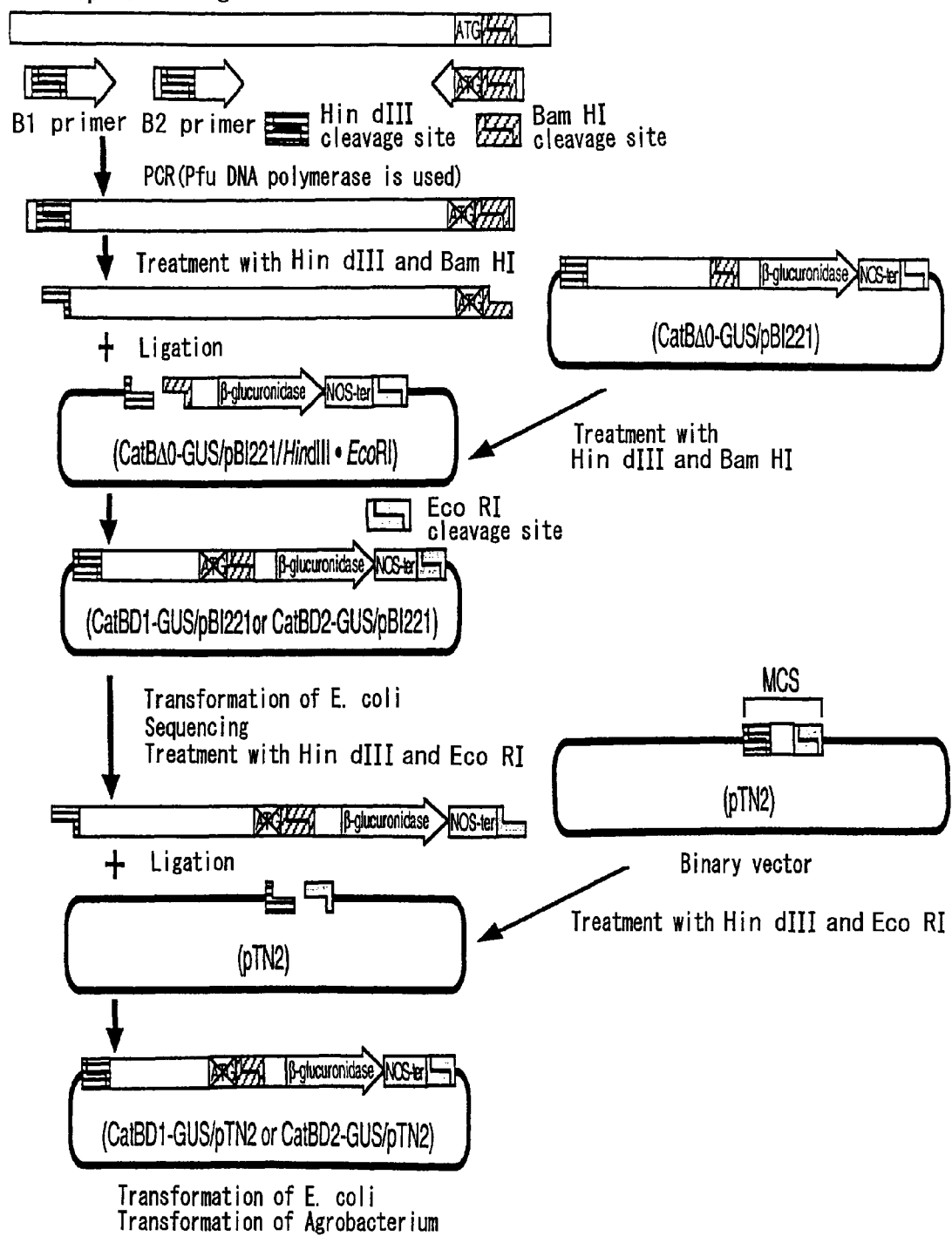
FIG. 2 shows a method for producing B1 (=CatBD1-GUS/pTN2) and B2 (=CatBD2-GUS/pTN2).

Specifically, various DNA fragments produced by deleting 5'-side regions from the CatB gene promoter region BΔ0 were fused with a reporter gene (GUS) and then introduced into a vector (FIGS. 1 and 2). The vector was introduced into rice and *Arabidopsis* for transformation. Various tissues of the first generation redifferentiated plants or subsequent generation plants was subjected to GUS tissue staining to investigate an expression site.

Figure 3:
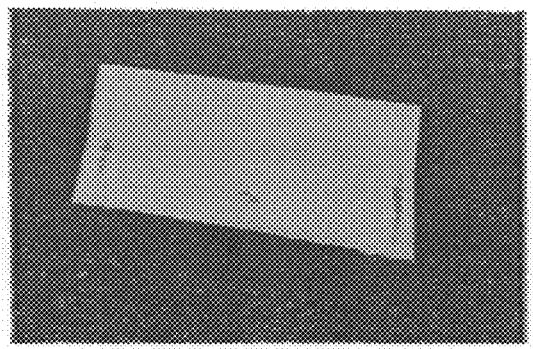
FIG. 3 is a photograph showing GUS staining of a young plant of rice having introduced B1 (To, redifferentiated first generation).
Figure 3:
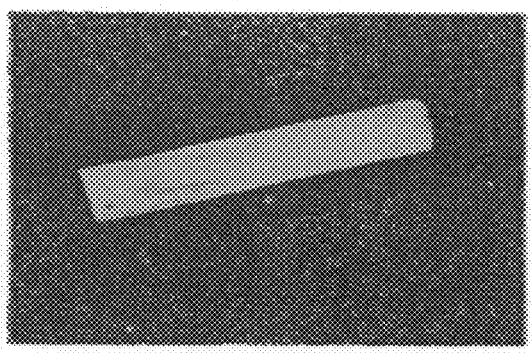
Figure 3:
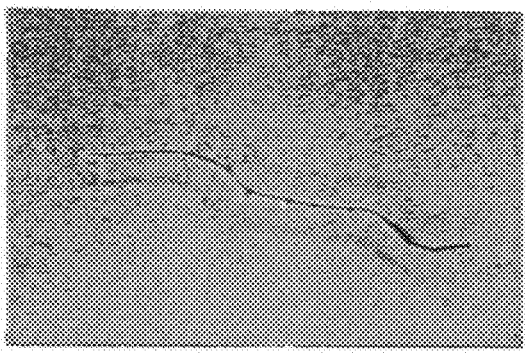
Figure 4:
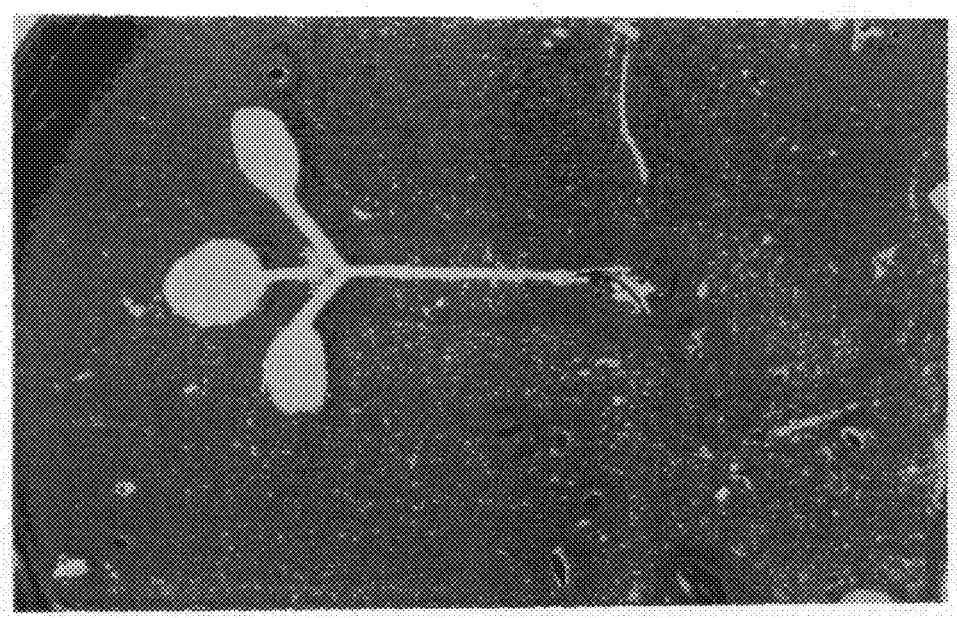
FIG. 4 is a photograph showing GUS staining of a young plant of *Arabidopsis* having introduced B1 (T2 generation) ((a) dark background; (b) bright background).
Figure 4:

As a result, it was revealed that even a short promoter DNA fragment (B1) of −329 to +298 upstream of the cDNA starting point (+1) (SEQ ID No. 11) can cause the reporter gene to be expressed in roots of young rice plants (FIG. 3, Tables 2 and 3), and roots and stem apices of young *Arabidopsis* plants (FIG. 4, Table 4).

TABLE 2

Summary of GUS Staining of Young Plants of Rice (To, redifferentiated first generation)

| Site strongly stained | BΔ0-introduced rice | BΔ3-introduced rice | B1-introduced rice | B2-introduced rice |
|---|---|---|---|---|
| Root | 25 | 12 | 13 | 3 |
| Root, leaf sheath, leaf blade | 0 | 4 | 0 | 0 |
| Leaf sheath, leaf blade | 6 | ND | 12 | 9 |
| No stain | 4 | 0 | 2 | 4 |
| Total | 35 | 16 | 27 | 16 |

Numrical figures: the number of individuals;
ND = Not determined (no investigation)

TABLE 3

Summary of GUS Staining of Flowering-stage Plants of Rice (To, redifferentiated first generation)

| Site strongly stained | BΔ0-introduced rice | BΔ3-introduced rice | B1-introduced rice | B2-introduced rice |
|---|---|---|---|---|
| Root | 0 | 0 | 2 | 1 |
| Root, leaf sheath, leaf blade | 3 | 1 | 1 | 0 |
| Leaf sheath, leaf blade | 8 | 3 | 8 | 7 |
| No stain | 0 | 2 | 1 | 2 |
| Total | 11 | 6 | 12 | 10 |

TABLE 4

Summary of GUS staining of Young Plants of *Arabidopsis* (T2 generation)

| Stained site | B1-1 | B1-2 | B1-3 | B1-4 | B1-5 | B2-3 | B2-4 | B2-5 | B2-6 | B2-8 |
|---|---|---|---|---|---|---|---|---|---|---|
| Root only | | | | | | | | | | |
| Stem apex only | | | | | | | 13 | 8 | | 9 |
| Root, stem apex | 1 | 23 | 7 | 20 | 19 | | | | 1 | 1 |
| Root, stem apex, other organs | 7 | | 6 | | | | | | 1 | |
| Stem apex, other organs | | | | | | | 5 | 9 | 12 | 4 |
| Other organs | | | | | | | | 7 | | |
| No stain | 4 | 2 | 8 | 6 | 1 | 24 | 6 | | 10 | 10 |
| Total | 12 | 25 | 21 | 26 | 24 | 24 | 24 | 24 | 24 | 24 |

The magnitude of organ specificity of expression varies between transformation plant individuals, though in about half of first generation redifferentiated rice plants having the introduced B1::GUS construct (B1 in FIG. 1), the reporter gene was strongly expressed in roots. It is considered that for rice, similarly, the reporter gene was strongly expressed in stem apices.

The expression specificity for roots of young rice plants is decreased as a 5'-side increasingly larger region of the promoter region is deleted. BΔ0 (71%)=BΔ3 (75%)>B1 (48%) >B2 (19%) are in order from the highest expression specificity (Table 2). The longer the promoter region, the stronger the expression specificity. Even from B1, it is possible to obtain a plant body performing specific expression if a desired plant is screened from a group of redifferentiated individuals. Therefore, BΔ0, BΔ3, or B1 can be selected depending on the purpose.

The promoter (B2) lacking −329 to −227 (SEQ ID No. 12) has a much reduced expression level in roots of rice and *Arabidopsis* (Tables 2 and 4). Therefore, this −329 to −227 region is necessary for expression in roots. This region has no known cis element relating to expression in roots. It is highly possible that a novel cis element is present in this region.

According to this result, a method has been developed, in which various sequences having a length of up to about 630 bases of the 1,364-base promoter region derived from the rice catalase CatB gene previously filed as a patent application, can be used to express a foreign gene in roots and stem apices in young plants of monocotyledons (e.g., rice and the like) and dicotyledons (e.g., *Arabidopsis* and the like).

In general, the conservativeness of the base sequence of a promoter is low. It is not easy to detect a promoter having a similar level of activity by screening using a promoter base sequence of several hundred bases. The conservativeness of a site (cis element) of a promoter region, to which a transcription regulatory factor (protein) binds is high. Therefore, by searching a cis element data base using a computer based on a specific sequence of the present invention, a number of cis element candidates are obtained. It is believed that bioinformatics techniques can be used to determine which cis element candidate actually functions.

Hereinafter, the present invention will be described by way of examples. The examples below are provided only for the purpose of illustration. Therefore, the scope of the present invention is not limited by the examples, except as by the accompanying claims.

EXAMPLES

Example 1

Isolation of Rice Catalase CatB Gene

A method of isolating the rice catalase CatB gene is described in Japanese Patent No. 2955644, entitled "Rice CatB Gene Promoter" (Registration Date: July, 1999). Briefly, the method will be described.

(Screening from Genomic Library)

A portion of CatA cDNA was used for cloning of a CatB gene. An insert portion of λ phage (clone #51) containing non-full-length cDNA (3'-terminal 1.35 kbp of the full length of about 1.8 kbp where a total of about 450 bp of the 5'-untranslational region and some code regions are deleted) obtained during cloning of CatA cDNA was amplified by PCR. DNA was prepared from the same phage and was used as a template. As primers, λ gt11-Forward Primer and λgt11 Reverse Primer (Toyobo Co., Ltd.) were used. Products were purified using Centricon-100 (Amicon) to a concentration of 25 ng/10 μl and were used as probes for a multi-prime labeling method (Amersham).

A rice genomic DNA library (RICE Genomic Library) purchased from CLONTECH Laboratories Inc. (Palo Alto, Calif., US) was screened for the CatB gene as follows. Phage λEMBL-3 containing the genomic library was used to infect *E. coli* strain NM538 in accordance with a commonly used method, so that a phage plaque was formed. The phage plaques were transferred to nylon membrane so as to be allowed to hybridize to the above-described probes. Note that the probes were labeled with $^{32}P$.

Hybridization solution: 6×SSC-0.1% SDS, 5×Denhardt's, 100 μg/ml salmon sperm DNA; hybridization temperature: 65° C.; hybridization time: overnight.

Thereafter, the membrane was washed under the following relatively mild conditions. Wash conditions: 2×SSC-0.1% SDS, room temperature, 5 min+30 min; 1×SSC-0.1% SDS, 68° C., 1 hour.

After washing, the nylon membrane was subjected to autoradiography in accordance with a commonly used method so as to detect clones hybridizing to the probes. DNA was prepared from each phage which was confirmed to undergo hybridization.

The above-described phage DNA was digested with a combination of restriction enzymes, Sal I and Sca I. The digested products were separated by agarose gel electrophoresis. The separated DNA fragments were transferred to nylon membrane so as to be allowed to hybridize to the above-described CatA cDNA fragments as probes. The hybridization conditions were the same as above. The membrane was washed under the following conditions. Wash conditions: 2×SSC, room temperature, 5-10 min, 2 times; 2×SSC-0.1% SDS, 65° C., 30 min.

After washing, the nylon membrane was subjected to autoradiography in accordance with a commonly used method well known in the art so as to detect DNA fragments hybridizing to the probes.

There were a group of clones having substantially the same signal intensity and band pattern (i.e., they were inferred to have the same structure), and clones having only partially-matched band patterns. The former clones having substantially the same signal intensity and band pattern were considered to correspond to the CatA gene. Actually, clone No. 74 was a gene corresponding to the CatA cDNA. On the other hand, the latter clones having only partially-matched band patterns were possibly clones lacking the CatA gene or clones of a catalase gene other than CatA. Therefore, CatA cDNA was used as a probe to perform hybridization under the following mild conditions or stringent conditions, and the resultant patterns were compared with each other.

Mild hybridization conditions 50% formamide-added, 6×SSC-0.1% SDS, 5×Denhardt's, 100 μg/ml salmon sperm DNA; hybridization temperature: 37° C.: hybridization time: overnight.

Wash conditions for the membrane were the same as above: 2×SSC-0.1% SDS, room temperature, 5 min+30 min; 1×SSC-0.1% SDS, 68° C., 1 hour.

Stringent hybridization conditions: 50% formamide-added, 6×SSC-0.1% SDS, 5×Denhardt's, 100 μg/ml salmon sperm DNA; hybridization temperature: 42° C.; hybridization time: overnight.

Wash conditions for the membrane: 2×SSC-0.1% SDS, room temperature, 5 min+30 min; 1×SSC-0.1% SDS, 68° C., 1 hour.

As a result of hybridization under the stringent conditions, the same number of bands as that for standard hybridization were detected. On the other hand, hybridization under the mild conditions showed a number of bands greater than that of the hybridization under the stringent conditions. According to these results, it was found that the clones having only partially-matched band patterns were highly possibly DNA, which is similar to CatA and has a partially different base sequence, i.e., a catalase gene other than CatA, but were not CatA gene-lacking clones.

About 20 clones having only partially-matched band patterns were considered candidates for catalase isoenzyme genes and were further analyzed. Among these clones, clone No. 7 was concluded to be a catalase gene different from CatA according to detailed Southern analysis, partial base sequence analysis, PCR analysis based on the CatA base sequence, and the like. It was also found that clone No. 7 has a different sequence from the sequence of CatB cDNA, and was designated as CatC. The base sequence of CatC is described in The Journal of Japan Society for Bioscience, Biotechnology, and Agrochemistry 68, 404(1994).

There were clones having a pattern different from those of CatA and clone No. 7 (CatC). Among the clones, clone No. 6 was analyzed in more detail. The base sequence of DNA of clone No. 6 was also partially analyzed. This sequence matched a cDNA sequence of the CatB gene (Plant Physiol. (1994) 105:1015-1016).

Based on the above-described information, two DNA oligomers were synthesized in order to obtain a 5'-untranslational region of the CatB gene.

GGTCGATTCTCATCTCTCCCACAACAAATC: SEQ ID No. 6 (corresponding to 102-131 of CatB cDNA)

CAATGTCTCAGGGCTTCCACGCTCATGCAC: SEQ ID No. 7 (corresponding to 484-455 of CatB cDNA)

On the other hand, a rice cDNA library was prepared from callus. DNA of this cDNA library was used as template and the above-described two synthesized DNAs were used as primers to carry out PCR under standard conditions. After amplification, about 400-bp DNA fragments were obtained. These 400-bp DNA fragments were used as probes to screen again the above-described clones, which were considered the CatB gene. As a result, several hybridizable clones were obtained.

Among them, the above-described clone No. 6 had a 5'-upstream region of at least about 1 kbp upstream of the 400 bp obtained by PCR amplification, and the full length was at least about 5 kbp. This clone was designated clone U6. A restriction enzyme map of clone U6 was produced (not shown).

Fragments containing a 5'-upstream region of about 1 kbp (Sal I-Eco RI digested fragments) and their downstream fragments (Eco RI-Eco RI digested fragments) were cut out from clone U6, and were inserted into a vector (pUC18) for sequence analysis to produce a number of plasmids lacking stepwise increasingly larger 5' segments and 3' segments for determination of the base sequence. Therefore, the nucleic acid sequence of CatB (4985 bp) is indicated by SEQ ID No. 2.

Example 2

Construction of CatBΔ0 (−1066 to +298)-GUS/pBI121)

CatBΔ0 (−1066 to +298)-GUS/pBI121 was constructed as described in Japanese Patent No. 2955644 entitled "Rice CatB gene promoter". Briefly, this construction will be described below.

The obtained CatB gene was 4985 bp in length. Further, it was found that a first exon is present from 1073 to 1216 of SEQ ID No. 2; a second exon is present from 1333 to 1429; a third exon is present from 2341 to 2618; a fourth exon is present from 2970 to 3746; a fifth exon is present from 3968 to 4057; a sixth exon is present from 4252 to 4319; a seventh exon is present from 4410 to 4503; and an eighth exon is present from 4616 to 4881, and first to seventh introns are present between corresponding exons. Based on the above-described sequence, the promoter region was inferred to be a sequence located before 1073. This sequence information can be used to cut out the promoter region. A plasmid CatB-GUS-Δ0 having the rice CatB gene promoter was prepared below.

Clone U6 was cleaved with SalI and EcoRI to cut out a 2.3-Kbp fragment. This fragment was linked to pUC18 which had been cleaved with SalI and EcoRI. The resultant recombinant plasmid was digested with Eco47I (manufactured by Toyobo Co., Ltd.), and an about 2-kbp fragment was collected. This fragment was digested with the Klenow fragment of DNA polymerase and then with PstI. As a result, a fragment A having a sequence (corresponding to SEQ ID No. 2 from 7 to 1370) of clone U6 was obtained. This fragment A contained a sequence upstream of the first exon, the first exon, the first intron, and a portion of the second exon. The 5'-terminus of the fragment is PstI site and the 3'-terminus is a blunt end.

An expression vector pBI221 (Clonetech) for plant cells has the cauliflower mosaic virus (CaMV) 35S promoter, the β-glucuronidase (GUS) coding region, and the nopaline synthase terminator (NOST). This pBI221 was digested with PstI and SmaI, and PstI-SmaI large fragment B was collected. This large fragment Bis such that the CaMV 35S promoter region was removed from pBI221. The large fragment B was linked with fragment A having a sequence of 7 to 1370 of clone U6 to produce CatB-GUS-Δ0.

(Transformation of Rice Cells and Expression of GUS gene)

70 ml of AA medium having a composition below was placed in a 300-ml flask. Rice Oc cells were subjected to suspension culture while stirring mildly (90 rpm).

The composition of the AA medium (Mol. Gen. Genet. 161: 67-76(1978))

|  | Concentration (mg/l) |
| --- | --- |
| 1) Inorganic salts | |
| $MnSO_4 \cdot 4-6H_2O$ | 10 |
| $H_3BO_3$ | 3 |
| $ZnSO_4 \cdot 7H_2O$ | 2 |
| $Na_2MoO_4 \cdot 2H_2O$ | 0.25 |
| $CuSO_4 \cdot 2H_2O$ | 0.025 |
| $CoCl_2 \cdot 6H_2O$ | 0.025 |
| KI | 0.75 |
| $CaCl_2 \cdot 2H_2O$ | 150 |
| $MgSO_4 \cdot 7H_2O$ | 250 |
| $NaH_2PO_4 \cdot H_2O$ | 150 |
| KCl | 3,000 |
| 2) Iron component | |
| Fe-EDTA | 40 |
| 3) Vitamin•Organic components | |
| sucrose | 20,000 |
| nicotinic acid 1-thiamine hydrochloride | 10 |
| pyridoxine hydrochloride | 1 |
| myo-inositol | 100 |
| L-arginine | 177 |
| L-glycine | 7.5 |
| L-glutamine | 900 |
| L-aspartic acid | 300 |
| 4) Hormone acid | |
| 2,4-D | 1 |
| kinetin | 0.2 |
| GA3 | 0.1 |

10 ml of the culture was transferred to 70 ml of fresh medium every week. After transfer, day-5 cells were used to produce-protoplasts. The protoplasts were produced in accordance with a method described in Mol Gen. Genet 206: 408-413 (1987). The day-5 subcultured callus cell suspension was transferred to a plastic petri dish. The medium was removed by an aspirator. 20 ml of an enzyme solution (4% cellulase RS (Yakult), 1% macerozyme R10 (Yakult), 0.4 M mannitol, 0.5% $CaCl_2.2H_2O$, 0.5% Potassium Dextran Sulfate). The petri dish was covered with PARAFILM and placed at 28° C. in a dark place. After about 5 hours, the medium was subjected to nylon mesh filtration to remove undigested matter, followed by repeatedly washing.

The thus-obtained protoplast was suspended in an EP buffer solution (5 mM $MgCl_2$, 70 mM KCl, 0.1% MES, 0.4M mannitol; distilled water was added to pH 5.6; sterilization was carried out using a filter, Nature 338:274-276(1989)). A portion (0.5 ml) of the suspension was taken out and mixed with 20 μg/ml of the above-described plasmid DNA and 30 μl/ml of salmon sperm DNA. Thereafter, the mixture was subjected to electroporation (300 V/cm) in a disposal cuvette (distance between electrodes was 0.4 cm) using a GENE PULSER (BIO-RAD, CA), where the capacitance was 500 μF and the resistance was 100Ω. The protoplast was incubated on ice for 10 minutes. 1.5 ml of R2P-culture medium was added to the protoplast. The mixture was placed in a MILLICELL (MILLIPORE, CA). The MILLICELL was placed in a 6-cm plastic dish containing 5 ml of R2P medium (Plant Cell Physiol. 14:1113-1121(1973)). Nurse cells were added outside the MILLICELL. Culture was carried out at 28° C. in a dark place. The presence of the nurse cell had no influence on the expression of CatA-GUS-Δ0, CatB-GUS-Δ0, and CatC-GUS-Δ0.

The composition of the R2P medium

|  | (mg/l) |
|---|---|
| (1) Major components | |
| KNO$_3$ | 4000 |
| (NH$_4$)$_2$SO$_4$ | 335 |
| MgSO$_4$•7H$_2$O | 250 |
| CaCl$_2$•2H$_2$O | 150 |
| NaH$_2$PO$_4$•H$_2$O | 273 |
| (2) Minor components | |
| MnSO$_4$•4H$_2$O | 1.6 |
| ZnSO$_4$•7H$_2$O | 2.2 |
| CuSO$_4$•5H$_2$O | 0.125 |
| H$_3$BO$_3$ | 3.0 |
| NaMoO$_4$•2H$_2$O | 0.125 |
| Na$_2$EDTA | 7.5 |
| FeSO$_4$•7H$_2$O | 5.5 |
| (3) Organic components | |
| inositol | 100 |
| nicotinic acid | 1.0 |
| pyridoxine hydrochloride | 1.0 |
| thiamine hydrochloride | 10 |
| sucrose (g/l) | 137 |
| 2,4-D (mg/l) | 2.0 |
| pH 5.6 | |

The protoplast for activating GUS was treated basically as described in Rabo-manyuaru: Shokubutsu-idennshi-no-kino-kaiseki [Laboratory Manual: Analysis of Plant Gene Functions] (Masaki Iwabuti Toshiro Shimura, Maruzen, 1992, p. 55) as follows. After electroporation, the protoplast was cultured at 28° C. in a dark place for 4 days. The resultant protoplast was collected using a 1-ml Falcon pipette (#7521) and placed in a 1.5 ml microtube, followed by centrifugation at 9,000 rpm for 3 minutes at room temperature. The resultant pellet was preserved at −80° C. until analysis.

200 μl of extract buffer (50 mM sodium phosphate buffer (pH7.0), 10 mM Na2 EDTA, 0.1% TritonX-100, 0.1% Sodium Lauryl Sarcosine, 10 mM β-mercaptoethanol) was added to the frozen pellet in ice water for 5 minutes to allow to melt. The mixture was treated for 1 minute by an ultra-sonication apparatus (Branson SONIFIER model 250) under conditions: Output control 2 and Duty cycle 10%. After treatment, the mixture was centrifuged at 15,000 rpm at 4° C. for 20 minutes. The supernatant (protoplast extract) was collected and used as a sample for measuring GUS activity. The protein concentration of the sample was determined by a Bradford method (Anal. Biochem 72:248-254(1976)).

The GUS activity was measured in accordance with a method described in Jefferson et al. (supra). The endogenous GUS activity was minimized by adding 20% (v/v) methanol to the reaction solution. Results were obtained from at least two experiments, each of which included a triplicate (three samples) for the same experiment.

These results showed that the CatB gene promoter has a considerably high level of activity as compared to the controls, i.e., CaMV CatA and CatC promoters (not shown).

Example 3

Base Modification of Start Codon and Production of 5'-Upstream DNA Fragment (B1 Fragment, B2 Fragment) of CatB by a PCR Method, and Construction of Plasmid 5'-upstream DNA fragments (B1 fragment and B2 fragment) of rice catalase gene CatB having a point mutation in its start codon were produced by a PCR method. The B1 fragment (−329 to +298, the starting point of the cDNA is regarded as +1 (SEQ ID No. 11)) was produced by PCR amplification using CatBΔ0 (−1066 to +298)-GUS/pBI121 as a template, primers 3D3-F1 (5'-GTG AAG CTT TCG ATC ACG ATG AGC GAG-3' (SEQ ID No. 8), a primer for introducing a HindIII cleavage site into the vicinity of the 5'-terminus of a DNA fragment) and BD3-MR (5'-GTA GGG ATC CGT GGC GTG ATT TG-3' (SEQ ID No. 9), a primer for replacing T of the start codon ATG of CatB with C), and Pfu DNA polymerase (Promega).

The B2 fragment (−226 to +298) was produced by PCR amplification using primers 3D3-F2 (5'-GTT AAG CTT GTC TTA TCT CCT CGT GAT CC-3' (SEQ ID No. 10), a primer for introducing a HindIII cleavage site into the vicinity of the 5'-terminus of a DNA fragment) and BD3-MR.

The obtained DNA fragments were treated with restriction enzymes HindIII and BamHI and were then incorporated into an upstream region of the GUS gene of the vector CatBΔ0-GUS/pBI221 which had been treated with HindIII and BamHI using DNA ligation kit Ver. 2 (Takara Shuzo). The vector was introduced into competent high DH5 alpha (Toyobo Co., Ltd.), which was *E. coli* for transformation. The vector was purified from the *E. coli* and its base sequence was determined and confirmed. The vector was treated with restriction enzymes HindIII and EcoRI to be cut to a DNA fragment containing the B1 or B2 fragment, the GUS gene, and the nopaline synthase gene terminator (NOS-ter). This DNA fragment was incorporated to a binary vector TN2 (Fukuoka et al., Plant Cell Reports 19:815-820 (2000)) which had been treated with HindIII and EcoRI.

Example 5

Introduction a Gene into Plants pTN2 was introduced into rice (variety: Nipponbare) in accordance with a method described in Hiei et al. (Plant J. 6: 271-282 (1994)) and Toki (Plant Mol. Biol. Rep. 15: 16-21 (1997)) using *Agrobacterium* (EHA105).

pTN2 was introduced into *Arabidopsis* (variety: Columbia) by a method partially modified from a method described in "Moderu-shokubutsu-no-Jikken-Purotokoru For Ine Shiroinunazuha: Saibo-kogaku Bessatsu-shokubutsu-saibo-kogaku sirizu 4; Genatsu-Shitsujyunho-niyoru-Keishitsu-tenkan [Experimental Protocol for Model Plants For Rice and *Arabidopsis thaliana*: Cellular Engineering, Special Issue, Plant Cellular Engineering Series 4; Transformation by a vacuum infiltration method" (Takashi Araki) pp. 109-113 (Supervised by Ko Shimamoto and Kiyotaka Okada)".

Example 6

GUS Tissue Staining Method of Plants

The GUS activity was observed by a method partially modified from a method described in "Shokubutsu-no-saibo-wo-miru-jikken-purotokoru: Idenshihatsugen-kara-saibo-naikouzou kino-made; Saibo-kogaku Bessatsu-shokubutsu-saibo-kogakusirizu 62-3; Saibo-reberu-de-GUSkassei-wo-miru-hoho [Experimantal Protocol for Observing Plant Cells: From Gene Expression to Intracellular Structure Function; Cellular Engineering, Special Issue, Plant Cellular Engineering Series 62-3; Method for Observing GUS activity at Cellular Level], (Misa Takahashi and Hiromichi Morikawa), pp. 71-79 (supervised by Hiroho Fukuda, Mikio Nishimura, and Kenzo Nakamura).

① X-Gluc solution [100 mM phosphate buffer (pH7.0), 1 mM X-Gluc, 0.3 mM potassium ferricyanide, 0.3 mM potassium ferrocyanide, 0.2%-Triton-X100] was prepared.

② 500 μL of X-Gluc solution was dispensed into each well of a 24-well titer plate.

③ Each tissue or section of rice and *Arabidopsis* was placed in a well and treated at 28° C. for 16 hours.

④ The X-Gluc solution was removed. 70% ethanol was added for decolorization.

⑤ The 70% ethanol was removed, and the tissue section was immersed in 50% glycerol solution.

⑥ The tissue section was observed by a microscope or a stereoscopic microscope.

(Results)

The magnitude of organ specificity varies between individual transformed plants. Nevertheless, in about half of first generation redifferentiated rice plants having the introduced B1::GUS construct (B1 in FIG. 1), the reporter gene was strongly expressed in roots. For transformed *Arabidopsis*, the reporter gene was strongly expressed in roots and stem apices inmost of the *Arabidopsis* T2 generation having the introduced B1::GUS construct (B1 in FIG. 1).

INDUSTRIAL APPLICABILITY

By utilizing this promoter, it is possible to synthesize a resistance substance against nematodes or soil pathogens in roots; synthesize a substance promoting the development of roots in the roots; produce a gene recombinant plant in which expression of a selective marker in the redifferentiated plant body is limited to roots when the plant is young, so as to suppress the expression when the plant is matured; or the like. Further, the capability of expression in stem apices can be used to develop a technique for suppress gene expression in vigorously proliferating cells.

A portion of the base sequence of the CatB gene promoter region of the present invention can be used to express a foreign gene at at least one site of roots and stem apices. Therefore, this promoter is useful for development of a promoter specific to at least one site of roots and stem apices for breeding plants (e.g. rice and the like) by gene manipulation using a protein synthesized in at least one site of roots and stem apices or a substance secreted outside cells.

For example, by utilizing this promoter, it is possible to synthesize a resistance substance against nematodes or soil pathogens in roots; synthesize a substance promoting the development of roots in the roots; produce a gene recombinant plant in which expression of a selective marker in the redifferentiated plant body is limited to roots, so as to suppress the expression when the plant is matured; or the like.

The invention claimed is:

1. An isolated promoter consisting of a nucleotide sequence indicated by SEQ ID No. 11.

2. A method for expressing a desired foreign coding sequence in a root or a stem apex of a plant, comprising the steps of:
   (a) constructing a vector comprising the promoter of claim 1 operably linked to the desired foreign coding sequence; and
   (b) introducing the vector to the root or the stem apex of the plant.

3. A method according to claim 2, wherein the plant is a monocotyledon or a dicotyledon.

4. A method according to claim 2, wherein the plant is a monocotyledon.

5. A method according to claim 2, wherein the plant is rice, *Arabidopsis*, maize, wheat, barley, tomato, cucumber, eggplant, potato, lettuce, Japanese radish, or carrot.

6. A method according to claim 2, wherein the desired foreign coding sequence is a coding sequence encoding at least one polypeptide selected from the group consisting of a polypeptide capable of conferring resistance to disease or nematodes or soil pathogens, a peptide capable of promoting development of roots, and a selective marker for a redifferentiated plant body.

7. A method according to claim 2, wherein the desired foreign coding sequence is expressed in a tip portion of the roots.

8. A method according to claim 2, wherein the desired foreign coding sequence is expressed in a meristem region of a young monocotyledon plant.

9. A method according to claim 2, wherein the desired foreign coding sequence is expressed in a stem apex portion.

* * * * *

SEQUENCE LISTING

```
<160> NUMBER OF SEQ ID NOS: 12

<210> SEQ ID NO 1
<211> LENGTH: 1364
<212> TYPE: DNA
<213> ORGANISM: Oryza sativa

<400> SEQUENCE: 1
ctgcaggtca acggatctta tttttccatt ataatatata taataaataa atatatgttt      60
acttttatta tagtacttta aaagataaat ctatatatgt tgttctagtt cctttaaact     120
aaatattatt aaagttatta atggttaaag ttataaaagt ttgatatcaa actcgtccaa     180
aatgtcgatt aatatcgaac cggagcgagt acagtattag tagcaagtca gccacatggg     240
acatggccca catgcatgca cgtcgtatga acacaccgtg attctttgcc acttgcataa     300
tattctagca ctgctatact acacgacgac tgacggcgac gtcagttcag tttagtttgc     360
cgcatccatc gcgaaggcta ctctacccat cccatttttt tttaaaaaaa aatactataa     420
atctaaatat cttacattag atttgtatat tttaaagcaa agagaataat atgtagatat     480
aagtatgtac ctactcgctc gagcacaaga tcactgcaac aagcattgaa gatcgctcct     540
agcaatggtc tcaacttacc atgtaaacta agagcaacta taatgttttt cttttattag     600
gaatggttgc atcttatatt ttgagattga gaaaacacat atagaaatta tacaggattt     660
```

```
agcatttggg atgccggccg gattcctgat ttcccagtct ctggctttct ttttaaacaa    720
aaacgaaaaa agcagtgatc cgatcgatca cgatgagcga gctagtaagc tccaaaacaa    780
aatagagtac gtacgtataa tcctagagtc cggataataa taatccgttt ggttcgcgtt    840
aaaaaagtct tatctcctcg tgatccctt  ttttggatcg atccatgttc gtagtacgtg    900
acaagcacgc gcaccaaccg aagcaggtac ctgtgtcgct gcctgtgggc cccacacacc    960
ccaagacggc cattaataaa caaacacgac gtggacgaag agaagggagg ccggcaagaa   1020
gcatactagc acgctacgaa accccccttc tcttcgtccc caaattgcac tacaaaaaag   1080 gccgccccctt tcttctctcc tcgtccttat caccaccaat ccgatcctct tctcttctct   1140
tctcttcttc cccacatcca gttcgattct catctctccc acaacaaatc acgccatgga   1200
tccctacaag gtgccgcctt tcctgatttt tcttttcttc tagatcgatc gtcgatttgg   1260
tttggtttgg tttcttgatg cgctcatccc aatctgactg actcactgga ttcctcctcc   1320
ttgcagcatc ggccgtccag cgggagcaat tccaccttct ggac                    1364

<210> SEQ ID NO 2
<211> LENGTH: 4985
<212> TYPE: DNA
<213> ORGANISM: Oryza sativa

<400> SEQUENCE: 2
gtcgacctgc aggtcaacgg atcttatttt tccattataa tatatataat aaataaatat     60
atgtttactt ttattatagt actttaaaag ataaatctat atatgttgtt ctagttcctt    120
taaactaaat attattaaag ttattaatgg ttaaagttat aaaagtttga tatcaaactc    180
gtccaaaatg tcgattaata tcgaaccgga gcgagtacag tattagtagc aagtcagcca    240
catgggacat ggcccacatg catgcacgtc gtatgaacac accgtgattc tttgccactt    300
gcataatatt ctagcactgc tatactacac gacgactgac ggcgacgtca gttcagttta    360
gtttgccgca tccatcgcga aggctactct acccatccca tttttttta aaaaaaaata     420 ctataaatct aaatatctta cattagattt gtatatttta aagcaaagag aataatatgt    480
agatataagt atgtacctac tcgctcgagc acaagatcac tgcaacaagc attgaagatc    540
gctcctagca atggtctcaa cttaccatgt aaactaagag caactataat gttttctctt    600
tattaggaat ggttgcatct tatattttga gattgagaaa acacatatag aaattataca    660
ggatttagca tttgggatgc cggccggatt cctgatttcc cagtctctgg ctttcttttt    720
aaacaaaaac gaaaaagca gtgatccgat cgatcacgat gagcgagcta gtaagctcca    780
aaacaaaata gagtacgtac gtataatcct agagtccgga taataataat ccgtttggtt    840
cgcgttaaaa aagtcttatc tcctcgtgat ccctttttt ggatcgatcc atgttcgtag    900
tacgtgacaa gcacgcgcac caaccgaagc aggtacctgt gtcgctgcct gtgggcccca    960 cacccccaa gacggccatt aataaacaaa cacgacgtgg acgaagagaa gggaggccgg   1020
caagaagcat actagcacgc tacgaaaccc cccttctctt cgtccccaaa ttgcactaca   1080
aaaaaggccg ccccttttctt ctcctccgt cctttatcacc accaatccga tcctcttctc   1140
ttctcttctc ttcttcccca catccagttc gattctcatc tctccacaa caaatcacgc   1200 catggatccc tacaaggtgc cgcctttcc tgatttttctt ttcttctaga tcgatcgtcg   1260
atttggtttg gtttggtttc ttgatgcgct catcccaatc tgactgactc actggattcc   1320
tcctccttgc agcatcggcc gtccagcggg agcaattcca ccttctggac caccaactcc   1380
ggcgcccccg tctggaacaa caactccgcc ctcaccgtcg gagagcgagg tactgagctg   1440
```

```
ctccatcctc catcttcctc atctcttcct ccacgaatct atacttccta tcgatccatg    1500
tgctttatgt ctgcttagag gcgtatttgg gcttgcttcc atcatgatcc aatgttaact    1560
ttgagcgatc agatgcttaa taatttgtct gtgtctggta gcaacagaaa aggtccctgg    1620
atctgtgtga attggactgt agcacgacgt gtgcgatctt gccttactat tgttccttta    1680
gagctattca aagtttgcat cttttggtgt ggggggtttt cagccttttg ctttgagtaa    1740
catgtccttg tcactacctt gtgattcatc tgtgctgctt acacacaaag aggaagatct    1800
ctagtttggt tgcactatgt tcttgttatt gctcggttac actccttcat caacgctaaa    1860
agacgcagtc ttgatatttt tctctgtcgc tgtcaatctg tcataccatt aataaagaac    1920
gtataaaaat tgaccttttc cccattcata gtagtgatta tctcacttgt cctcagttct    1980
aaaacagcat tcttgttttt tgggggtttt tttaccatta tcggttcact ttacaaagta    2040
atctgatgac gatcaaattt actggagtac cagagaagca caagtctatt tcatacatat    2100
atccaacatg actcaagttt cgaaagtgac tggaagtcat gttccaaatg tcatggtcac    2160
taaaagtacc aaactctgac aaagatgtat ttgcatctag aactaagtgc ttctatcatc    2220
gatctgtgaa gttttctttc tagtgttttc cctttattta tactcagcaa ctcctgtatt    2280
tttgcaatct gtaatcatgg ctgttttgtg gtttgacatg atgaattctt caatcgacag    2340
gccctatcct ccttgaggac tatcatctga ttgaaaagct tgcacagttt gacagggagc    2400
gtatccctga acgtgtcgtt catgcaaggg gagccagtgc caagggattt tttgaggtta    2460
ctcatgatat ttctcacctc acatgtgctg attttctccg tgctcctggt gttcagaccc    2520
cagttattgt tcggttctcc acagtcgtgc atgagcgtgg aagccctgag acattgaggg    2580
aaccacgtgg ttttgctgtc aagttttaca ctagagaggg acttgctctt tcgcttcttt    2640
ctttcatagg attgtaggag ggagacattc agtataatgt attcttcaag cataaggctg    2700
tagaatcaaa tgtctagttg ttctcagttg gttaagtaga acatgaaaga ttggttgtcc    2760
tttacctcca cactccatag gtccagtgca ttgcttaatc ttatatctac taaagcaaat    2820
gagggtaatt tggtcttata tatctcaaaa gtctcacaca ttggacatat atctaaccag    2880
tgtcacctac aactttgtct tactgtttat ttactgattt gcattcagtg ctgccatatt    2940
ttgatatttt ctgagtcaat gcttttcagg gtaattttga tcttgttggg aacaatatgc    3000
ctgtcttttt tatccgagat gggatgaaat tccctgacat ggtccatgct ttcaagccaa    3060
gtccaaagac caatatgcag gagaactgga gaatagttga tttcttttca caccacccag    3120
agagcctgca catgttctcc ttcctctttg acgatgtagg catcccactc aaccacaggc    3180
acatggaggg ttttggtgtc aacacctaca ccctaatcaa taaggatgga aagcctcacc    3240
ttgtcaaatt ccactggaag cctacctgtg gtgtcaaatg cctgttggat gatgaagctg    3300
tgactgttgg cggcacctgc cacagccatg ccacgaagga cttgactgat tctattgcag    3360
cagggaatta cccagagtgg aagctttaca tccagactat tgatcctgat catgaggaca    3420
gatttgactt cgatcctctt gatgtcacca agacatggcc agaggatatc atccccctgc    3480
agccagttgg acggatggtc ctgaacaaaa acattgataa cttctttgca gaaaatgaac    3540
agcttgcttt ctgcccagcg ataattgtcc ctggaatcca ttactctgat gataagctgc    3600
tccagacaag aattttctcc tatgctgata cccaaaggca ccgtcttggc ccaaactatt    3660
tgatgcttcc tgtgaatgca ccaaaatgtg cataccacaa caaccaccac gatggctcca    3720
tgaatttcat gcacagggat gaagaggtac tgtgtgtata tactttcaga gatacatctc    3780
```

-continued

```
ctgcattcag ttgttgtgat gcatctttct gtttttgtcc attacatatt gtttcttcca      3840
gtcaacacaa acagaatggg actatcattc agtttattgc atttacatct atttgccttg      3900
tttttaggtt aactacttcc cttcaattca gtttattgca tttacatcta tttgccttgt      3960
tttttaggtt aactacttcc cttcaaggtt tgatgctgca cgtcatgctg agaaggtccc      4020
tattcctcct cgtgttctaa caggctgtcg ggaaaaggtg tgtaacttgg tccacttgaa      4080
ctccttgcgc tgttaccttg tgagcatggt tttgtcccgc tacattagga gactatttgc      4140
tgatttggaa tgcgatgaaa tatgtattat agatgtggta ccctggaaag tacaatgacc      4200
acatgcattt gacacaatgt tttctgcctc tcttttttgt tggaaatgca gtgtgtcatt      4260
gacaaggaga acaatttcca acaggctggt gagagatacc ggtcatttga ccctgccagg      4320
tttgttcttg ttcaatttaa ttcgtgtgaa cacatcgaag agtttgagca acaacgctaa      4380
ttaaactttt cttttgtat gtaacacagg caagatcgtt ttctccagcg gtgggttgat      4440
gctctctcag atcctcgtat tacacatgaa ctccgtggca tctggatctc ctactggtcg      4500
caggtaacat aatttcttcg tgggtgcaaa gtgcttatca gttgtcagtg agagatcatg      4560
tacaattgta ccttgtattg acacactgaa accatatatt tgtgtgttgt tgcagtgtga      4620
tgcgtccctt gggcagaagc tggcttcacg tctcaacctg aaaccaaaca tgtagatcgg      4680
ccaggaggaa tccagtggtg gtgctatgtt ggacagtcaa acatgaactg taatgtgtcg      4740
accagccgta gtcgtgaata aaatgtgata cggtgatatg tatactggtg acgcaagttg      4800
tgaaactgta tctggaatcc tgaaaatatg ccttgctgtg tcttgggaaa gagataataa      4860
agactgatac agtgggtgct atatgtttga acttgtttat acatctgcca tctcttgttt      4920
gcctttgtgt taagatggct ttagagactg gaacgaacaa ccagctgttt gccttttgtgc     4980 cttttg                                                                 4985
```

<210> SEQ ID NO 3
<211> LENGTH: 866
<212> TYPE: DNA
<213> ORGANISM: Oryza sativa

<400> SEQUENCE: 3

```
tcgagcacaa gatcactgca acaagcattg aagatcgctc ctagcaatgg tctcaactta       60
ccatgtaaac taagagcaac tataatgttt ttcttttatt aggaatggtt gcatcttata      120
ttttgagatt gagaaaacac atatagaaat tatacaggat ttagcatttg ggatgccggc      180
cggattcctg atttcccagt ctctggcttt cttttaaac aaaaacgaaa aaagcagtga       240
tccgatcgat cacgatgagc gagctagtaa gctccaaaac aaaatagagt acgtacgtat      300
aatcctagag tccggataat aataatccgt ttggttcgcg ttaaaaaagt cttatctcct      360
cgtgatccct ttttttggat cgatccatgt tcgtagtacg tgacaagcac gcgcaccaac      420
cgaagcaggt acctgtgtcg ctgcctgtgg gccccacaca ccccaagacg gccattaata      480
aacaaacacg acgtggacga agagaaggga ggccggcaag aagcatacta gcacgctacg      540 aaaccccccct tctcttcgtc cccaaattgc actacaaaaa aggccgcccc tttcttctct      600
cctcgtcctt atcaccacca atccgatcct cttctcttct cttctcttct tccccacatc      660
cagttcgatt ctcatctctc ccacaacaaa tcacgccatg gatccctaca aggtgccgcc      720
ttttcctgat tttcttttct tctagatcga tcgtcgattt ggtttggttt ggtttcttga      780
tgcgctcatc ccaatctgac tgactcactg gattcctcct ccttgcagca tcggccgtcc      840
agcgggagca attccacctt ctggac                                           866
```

<210> SEQ ID NO 4
<211> LENGTH: 627
<212> TYPE: DNA
<213> ORGANISM: Oryza sativa

<400> SEQUENCE: 4

```
aagctttcga tcacgatgag cgagctagta agctccaaaa caaaatagag tacgtacgta      60
taatcctaga gtccggataa taataatccg tttggttcgc gttaaaaaag tcttatctcc     120
tcgtgatccc ttttttgga tcgatccatg ttcgtagtac gtgacaagca cgcgcaccaa     180
ccgaagcagg tacctgtgtc gctgcctgtg ggccccacac accccaagac ggccattaat     240
aaacaaacac gacgtggacg aagagaaggg aggccggcaa gaagcatact agcacgctac     300
gaaaccccc ttctcttcgt ccccaaattg cactacaaaa aaggccgccc ctttcttctc     360
tcctcgtcct tatcaccacc aatccgatcc tcttctcttc tcttctcttc ttccccacat     420
ccagttcgat tctcatctct cccacaacaa atcacgccac ggatccctac aaggtgccgc     480
cttttcctga ttttcttttc ttctagatcg atcgtcgatt tggtttggtt tggtttcttg     540
atgcgctcat cccaatctga ctgactcact ggattcctcc tccttgcagc atcggccgtc     600
cagcgggagc aattccacct tctggac                                          627
```

<210> SEQ ID NO 5
<211> LENGTH: 524
<212> TYPE: DNA
<213> ORGANISM: Oryza sativa

<400> SEQUENCE: 5

```
aagcttgtct tatctcctcg tgatcccttt ttttggatcg atccatgttc gtagtacgtg      60
acaagcacgc gcaccaaccg aagcaggtac ctgtgtcgct gcctgtgggc cccacacacc     120
ccaagacggc cattaataaa caaacacgac gtggacgaag agaagggagg ccggcaagaa     180
gcatactagc acgctacgaa accccccttc tcttcgtccc caaattgcac tacaaaaaag     240
gccgccccctt tcttctctcc tcgtccttat caccaccaat ccgatcctct tctcttctct     300
tctcttcttc cccacatcca gttcgattct catctctccc acaacaaatc acgccacgga     360
tccctacaag gtgccgcctt ttcctgattt tcttttcttc tagatcgatc gtcgatttgg     420
tttggtttgg tttcttgatg cgctcatccc aatctgactg actcactgga ttcctcctcc     480
ttgcagcatc ggccgtccag cgggagcaat tccaccttct ggac                       524
```

<210> SEQ ID NO 6
<211> LENGTH: 30
<212> TYPE: DNA
<213> ORGANISM: Oryza sativa

<400> SEQUENCE: 6

```
ggtcgattct catctctccc acaacaaatc                                        30
```

<210> SEQ ID NO 7
<211> LENGTH: 30
<212> TYPE: DNA
<213> ORGANISM: Oryza sativa

<400> SEQUENCE: 7

```
caatgtctca gggcttccac gctcatgcac                                        30
```

<210> SEQ ID NO 8

```
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 8
gtgaagcttt cgatcacgat gagcgag                                          27

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 9
gtagggatcc gtggcgtgat ttg                                              23

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 10
gttaagcttg tcttatctcc tcgtgatcc                                        29

<210> SEQ ID NO 11
<211> LENGTH: 627
<212> TYPE: DNA
<213> ORGANISM: Oryza sativa

<400> SEQUENCE: 11
atccgatcga tcacgatgag cgagctagta agctccaaaa caaaatagag tacgtacgta      60
taatcctaga gtccggataa taataatccg tttggttcgc gttaaaaaag tcttatctcc     120
tcgtgatccc ttttttttgga tcgatccatg ttcgtagtac gtgacaagca cgcgcaccaa    180
ccgaagcagg tacctgtgtc gctgcctgtg ggcccacac accccaagac ggccattaat      240
aaacaaacac gacgtggacg aagagaaggg aggccggcaa gaagcatact agcacgctac    300 gaaaccccc ttctcttcgt ccccaaattg cactacaaaa aaggccgccc ctttcttctc     360
tcctcgtcct tatcaccacc aatccgatcc tcttctcttc tcttctcttc ttccccacat    420
ccagttcgat tctcatctct cccacaacaa atcacgccat ggatccctac aaggtgccgc    480
cttttcctga ttttcttttc ttctagatcg atcgtcgatt tggtttggtt tggtttcttg    540
atgcgctcat cccaatctga ctgactcact ggattcctcc tccttgcagc atcggccgtc    600
cagcgggagc aattccacct tctggac                                         627

<210> SEQ ID NO 12
<211> LENGTH: 103
<212> TYPE: DNA
<213> ORGANISM: Oryza sativa

<400> SEQUENCE: 12
atccgatcga tcacgatgag cgagctagta agctccaaaa caaaatagag tacgtacgta      60
taatcctaga gtccggataa taataatccg tttggttcgc gtt                       103
```